United States Patent [19]
Ishizaki et al.

[11] Patent Number: 5,234,894
[45] Date of Patent: Aug. 10, 1993

[54] CARBONYL ACETONITRILE DERIVATIVE AND HERBICIDE CONTAINING IT AS AN ACTIVE COMPONENT

[75] Inventors: Masahiko Ishizaki; Seiji Nagata; Tadashi Kobutani, all of Tsukuba, Japan

[73] Assignee: Tokuyama Soda Kabushiki Kaisha, Tokuyama, Japan

[21] Appl. No.: 858,509

[22] Filed: Mar. 27, 1992

[30] Foreign Application Priority Data
Mar. 29, 1991 [JP] Japan ................................ 3-89102

[51] Int. Cl.$^5$ ............... A01N 43/48; A01N 37/34; A01N 43/00; A01N 43/02; A01N 43/36; A01N 43/40; C07C 69/76; C07C 225/00
[52] U.S. Cl. .................... 504/224; 504/227; 504/235; 504/242; 504/247; 504/254; 504/256; 504/259; 504/265; 504/267; 504/277; 504/283; 504/284; 544/137; 544/286; 544/315; 544/318; 544/354; 546/275; 546/290; 546/300; 546/301; 546/302; 548/547; 549/63; 549/466; 558/389; 558/396; 558/405; 558/410; 504/289; 504/298; 504/299
[58] Field of Search ............... 558/389, 396, 405, 410; 544/286, 315, 318, 354, 137; 546/114, 115, 116, 157, 158, 275, 290, 300, 301, 302; 548/170, 229, 327, 543, 547; 549/63, 466; 71/88, 90, 92, 94, 95, 105; 504/224, 267, 277, 283, 284, 289, 298, 299, 227, 235, 242, 247, 254, 256, 259, 265

[56] References Cited
U.S. PATENT DOCUMENTS

| | | | |
|---|---|---|---|
| 3,846,470 | 11/1974 | Raabe et al. | 558/405 X |
| 3,865,863 | 2/1975 | Field et al. | 558/405 |
| 3,937,722 | 2/1976 | Heine et al. | 558/405 |
| 4,010,190 | 3/1988 | Davis et al. | 558/405 |
| 4,218,468 | 8/1980 | Paul | 558/405 X |
| 4,233,054 | 11/1980 | Szczepanski et al. | 558/389 |
| 4,596,883 | 6/1986 | Schwindeman et al. | 558/405 X |
| 4,715,882 | 12/1987 | Raju | 558/389 X |
| 4,988,385 | 1/1991 | Gilkerson et al. | 558/405 X |

FOREIGN PATENT DOCUMENTS
0604961 9/1960 Canada .................. 558/405

OTHER PUBLICATIONS
Showa, Chemical Abstracts, vol. 102, #220444n (1985).

Primary Examiner—Floyd D. Higel
Attorney, Agent, or Firm—Sherman and Shalloway

[57] ABSTRACT

A cyanoketone derivative of the following formula (1)

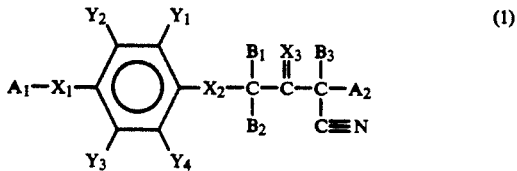

wherein $A_1$ is a substituted or unsubstituted phenyl or naphthyl group or a substituted or unsubstituted heterocyclic group;
each of $X_1$, $X_2$ and $X_3$ is independently an oxygen or sulfur atom;
each of $B_1$, $B_2$ and $B_3$ is independently a hydrogen atom or $C_1$–$C_6$-alkyl group;
each of $Y_1$, $Y_2$, $Y_3$ and $Y_4$ is independently a hydrogen atom, a halogen atom or a $C_1$–$C_6$-alkyl group; and
$A_2$ is a substituted or unsubstituted group selected from the group consisting of a $C_1$–$C_6$-alkyl group, a $C_2$–$C_6$-alkenyl group, a $C_2$–$C_6$-alkynyl group, a $C_1$–$C_4$-alkoxy group, a $C_1$–$C_4$-alkylthio group, a $C_1$–$C_6$-alkoxycarbonyl group, an unsubstituted benzoyl group, a halogen-substituted benzoyl group, a cyano group or a group as defined in $A_1$;
provided that when $B_1$ is a hydrogen atom and $B_2$ is alkyl, the compound of the formula (1) is an R- or S-enantiomer with regard to asymmetric carbon to which $B_1$ and $B_2$ are bonded, or a mixture of these enantiomers. The cyanoketone derivative has a remarkably high herbicidal activity and is effective against a variety of gramineous weeds.

9 Claims, No Drawings

CARBONYL ACETONITRILE DERIVATIVE AND HERBICIDE CONTAINING IT AS AN ACTIVE COMPONENT

DETAILED DESCRIPTION OF THE INVENTION

The present invention relates to a cyanoketone derivative and a herbicide containing it as an active component.

A variety of compounds have been tested on their herbicidal activities, and many herbicidal compounds are commercially available.

Japanese Laid-open Patent Application No. 54525/1974 discloses that a herbicide prepared by combining a compound of the following formula (2)

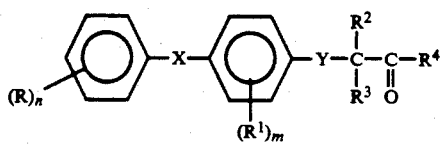

wherein R is H, halogen, $C_1 \sim C_4$ alkyl, $C_1 \sim C_4$ alkoxy or alkylthio, cyclohexyl, cyclopentyl or phenyl, $R^1$ is H, halogen, $C_1 \sim C_4$ alkyl or $C_2 \sim C_4$ alkenyl, each of X and Y is oxygen or sulfur, each of n and m is an integer of 1 to 30, $R^2$ is H, $C_1 \sim C_{10}$ alkyl, $C_2 \sim C_6$ alkoxyalkyl, $C_2 \sim C_4$ alkylamine or phenyl, $R^3$ is H or $C_1 \sim C_4$ alkyl, $R^4$ is —OH, —O—$C_1 \sim C_{10}$ alkyl, —S—$C_1 \sim C_6$ alkyl, —O—$C_2 \sim C_4$ alkenyl, —O—cyclohexyl, —O—cyclopentyl, phenoxy or phenylthio which may be substituted with one or two halogen atoms, —$NH_2$, —NH—$C_1 \sim C_4$ alkyl, —N-di($C_1 \sim C_4$)alkyl,

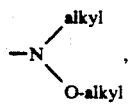

halogen, —$CF_3$, —NH—phenyl substituted with —$OCF_2CF_2H$ or —$COOCH_3$, —O—benzyl, —NH—benzyl, —S—benzyl or —O—kat (kat is an inorganic or organic cation), for example, the compound of the following formula (3)

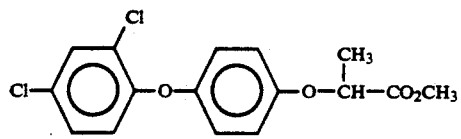

(commercially available under the trade name of "Hoelon") with an auxiliary exhibits an effect on grasses (gramineous plants).

Ex-West Germany Laid-open Patent Application No. 2,812,571 and its corresponding Japanese Laid-open Patent Application No. 22371/1979 disclose that the trifluoromethylpyridoxyphenoxypropionic acid derivative of the following formula (4)

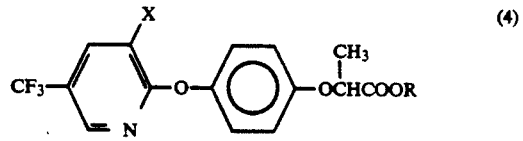

wherein X is H or Cl, R is H, lower alkyl, lower alkenyl, cycloalkyl, a salt-forming atom or a salt-forming moiety, for example, the compound of the following formula (5)

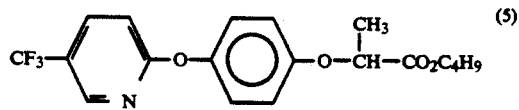

(commercially available under the trade name of "Fusilade"), exhibits a herbicidal effect on gramineous weeds.

On the other hand, Japanese Laid-open Patent Application No. 11452/1985 discloses α-cyanoketones of the following formula (6)

which are a compound of the above formula (6) in which $R_1$ is an alkyl group or an aromatic group and $R_2$ is an alkyl group having at least 3 carbon atoms, an aralkyl group, an aromatic group or a heterocyclic group and a compound of the formula (6) in which $R_1$ is a heterocyclic group, a substituted phenoxy or substituted thiophenoxy group and $R_2$ is a hydrogen atom, an alkyl group, an aromatic group or a heterocyclic group, and that such α-cyanoketones exhibit an effect on a variety of weeds such as southern crabgrass, barnyardgrass, tufted knotweed and slender amaranth when these are applied in a high dosage (foliar application test).

It is an object of the present invention to provide a novel cyanoketone derivative.

It is another object of the present invention to provide a herbicide containing the cyanoketone derivative of the present invention as a herbicidal active component.

It is further another object of the present invention to provide a novel cyanoketone derivative which exhibits high selectivity and high herbicidal activity and a herbicide containing this derivative.

It is still further another object of the present invention to provide a herbicide which has high herbicidal activity on grasses even when used in a low dosage and which is much safe even when applied to intended crop in a high dosage.

Other objects and advantages of the present invention will be apparent from the following description.

According to the present invention, the above objects and advantages of the present invention are achieved, first, by a cyanoketone derivative of the following formula (1)

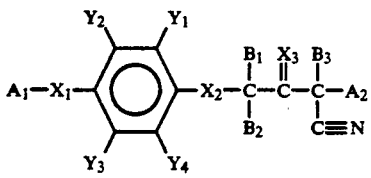

(1)

wherein $A_1$ is a substituted or unsubstituted aromatic group or a substituted or unsubstituted heterocyclic group, each of $X_1$, $X_2$ and $X_3$ is independently an oxygen or sulfur atom, each of $B_1$, $B_2$ and $B_3$ is independently a hydrogen atom or alkyl, each of $Y_1$, $Y_2$, $Y_3$ and $Y_4$ is independently a hydrogen atom, a halogen atom or alkyl, and $A_2$ is substituted or unsubstituted alkyl, alkenyl, alkynyl, alkoxy, alkylthio, alkoxycarbonyl, substituted or unsubstituted benzoyl, cyano, a substituted or unsubstituted aromatic group or a substituted or unsubstituted heterocyclic group, provided that when $B_1$ is a hydrogen atom and $B_2$ is alkyl, the compound of the formula (1) is any one of two enantiomers with regard to asymmetric carbon to which $B_1$ and $B_2$ are bonded, or a mixture of these in arbitrary proportion.

In the above formula (1), $A_1$ is a substituted or unsubstituted aromatic group, or a substituted or unsubstituted heterocyclic group.

The aromatic group preferably includes phenyl and naphthyl.

The heterocyclic group preferably includes five-membered or six-membered cyclic groups having at least one hetero atom selected from the group consisting of oxygen, sulfur and nitrogen atoms.

Examples of such heterocyclic groups preferably include five-membered cyclic groups such as furyl, thienyl, pyrrolyl, imidazolyl, pyrazolyl, oxazolyl, thiazolyl, isooxazolyl and isothiazolyl groups; six-membered ring groups such as pyridyl, pyranyl, thiopyranyl, pyrazinyl, pyridinyl, triazinyl and cyclohexenyl groups; five- and six-membered fused ring groups such as benzofuranyl, benzothienyl, indolyl, benzimidazolyl, benzothiazolyl, benzoxazolyl, oxazolopyridinyl and thizolopyridinyl groups; and six- and six-membered fused ring groups such as quinolyl, quinoxalinyl and quinazolinyl groups.

The substituent which may be substituted on these aromatic and heterocyclic groups includes a halogen atom such as chlorine, bromine, iodine and fluorine; an alkyl group having 1 to 4 carbon atoms such as methyl, ethyl, propyl and butyl; a halogenoalkyl group such as chloromethyl, difluoromethyl, trifluoromethyl, trifluoroethyl, perfluoroethyl, pentachloropropyl and perfluorobutyl; an alkoxy group having 1 to 4 carbon atoms such as methoxy, ethoxy, propoxy and butoxy; an alkylthio group having 1 to 4 carbon atoms such as methylthio, ethylthio, propylthio and butylthio; an alkoxycarbonyl group having 1 to 6 carbon atoms such as methoxycarbonyl, ethoxycarbonyl, propoxycarbonyl and butoxycarbonyl; a nitro group; and a cyano group. These substituents are preferred particularly in an industrial point of view.

In the formula (1), each of $X_1$ and $X_2$ is, independently of the other, an oxygen or sulfur atom. In particular, an oxygen atom is preferred.

In the formula (1), each of $Y_1$, $Y_2$, $Y_3$ and $Y_4$ is, independently of the others, a hydrogen atom, a halogen atom or alkyl.

The halogen atom includes chlorine, bromine, iodine and fluorine. The alkyl may be linear or branched, and is preferably selected from an alkyl group having 1 to 6 carbon atoms such as methyl, ethyl, propyl, butyl, heptyl and hexyl.

In the formula (1), each of $B_1$, $B_2$ and $B_3$ is, independently of the others, a hydrogen atom or alkyl. The alkyl preferably include a linear or branched alkyl group having 1 to 6 carbon atoms. Examples of the alkyl group include those specified concerning $Y_1$.

In the formula (1), $A_2$ is substituted or unsubstituted alkyl, alkenyl, alkynyl, alkoxy, alkylthio, alkoxycarbonyl, substituted or unsubstituted benzoyl, cyano, a substituted or unsubstituted aromatic group or a substituted or unsubstituted heterocyclic group.

The alkyl preferably includes a linear or branched alkyl group having 1 to 6 carbon atoms. The alkenyl preferably includes a linear or branched alkenyl group having 2 to 6 carbon atoms. The alkynyl preferably includes a linear or branched alkynyl group having 2 to 6 carbon atoms. The alkoxy preferably includes a linear or branched alkoxy group having 1 to 4 carbon atoms. The alkylthio preferably includes a linear or branched alkylthio group having 1 to 4 carbon atoms. The alkoxycarbonyl preferably includes an alkoxy carbonyl group having 1 to 6 carbon atoms. The aromatic and heterocyclic groups and substitutents thereon are preferably selected from those specified concerning $A_1$.

The alkyl group includes those specified concerning $Y_1$.

The substituent which may be substituted on the alkyl preferably includes a halogen atom, an alkoxy group having 1 to 4 carbon atoms, an alkylthio group having 1 to 4 carbon atoms, a tetrahydrofuryl group and a cyano group.

The alkenyl group preferably includes ethenyl, propenyl, butenyl, pentenyl and hexenyl.

The alkynyl group preferably includes ethynyl, propynyl, butynyl, pentynyl and hexynyl.

The alkoxy group preferably includes methoxy, ethoxy, propoxy and buthoxy.

The alkylthio group preferably includes methylthio, ethylthio, propylthio and butylthio.

The alkoxycarbonyl group preferably includes methoxycarbonyl, ethoxycarbonyl, propoxycarbonyl and butoxycarbonyl.

The compound of the above formula (1) preferably include the following compounds.

(100) 1-cyano-1-(3-methoxyphenyl)-3-[4-(4-fluorophenoxy)-phenoxy]-acetone,
(102) 1-cyano-1-(3-trifluorophenyl)-3-[4-(3-trifluorophenoxy)-phenoxy]-2-butanone,
(103) 2-cyano-2-methyl-4-[4-(2,4-difluorophenoxy)-phenoxy]-3-pentanone,
(104) 2-cyano-2-methyl-4-[4-(2-chloro-4-methylphenoxy)-phenoxy]-3-hexanone,
(106) 1-cyano-1-(2,4-dichlorophenyl)-3-[4-(2-chloro-4-trifluoromethylphenoxy)-phenoxy]-2-butanone,
(108) 1-cyano-1-(3-trifluoromethylphenyl)-3-[4-(2-chloro-4-fluorophenoxy)-phenoxy]-2-butanone,
(110) 1-cyano-1-(N-methylpyrrolyl)-3-[4-(2-chloro-4-methylphenoxy)-phenoxy]-2-butanone,
(112) 1-cyano-1-(2-imidazolyl)-3-[4-(2-methyl-4-trifluoromethylphenylthio)-phenoxy]-3-methyl-2-butanone,
(114) 1,1-dicyano-3-[4-(4-trifluoromethylphenylthio)-phenoxy]-2-butanethione,
(116) 1-cyano-1-ethoxycarbonyl-3-[4-(2-fluoro-4-chlorophenoxy)-phenylthio]-2-butanone, (118) 1-cyano-1-(2,4-dichlorophenyl)-3-[4-(3-chloro-5-trifluoromethyl-2-pyridyloxy)-phenoxy]-2-butanone,
(120) 1-cyano-1-(2-imidazolyl)-3-[4-(3-chloro-5-trifluoromethyl-2-pyridyloxy)-phenoxy]-2-butanone,
(122) 1-cyano-1-(2-pyridyl)-3-[4-(3-chloro-5-trifluoromethyl-2-pyridyloxy)-phenoxy]-2-butanone,
(124) 1-cyano-1-(2-indolyl)-3-[4-(3-chloro-5-trifluoromethyl-2-pyridyloxy)-phenoxy]-2-butanone,
(126) 1-cyano-1-(2-quinolyl)-3-[4-(3-chloro-5-trifluoromethyl-2-pyridyloxy)-phenoxy]-2-butanone,
(128) 1-cyano-1-(2-fluorophenyl)-3-[4-(3-chloro-5-trifluoromethyl-2-pyridyloxy)-phenoxy]-3-methyl-2-butanone,
(130) 1-cyano-1-(3-trifluoromethylphenyl)-3-[4-(3-chloro-5-trifluoromethyl-2-pyridyloxy)-phenoxy]-3-methyl-2-butanone,
(132) 1-cyano-1-(3-trifluoromethylphenyl)-3-[4-(3-chloro-5-trifluoromethyl-2-pyridyloxy)-phenoxy]-2-butanone,
(134) 1-cyano-1-(2-chloro-4-methylphenyl)-3-[4-(5-trifluoromethyl-2-pyridyloxy)-phenoxy]-2-propanethione,
(136) 1-cyano-1-(2,4-dichlorobenzoyl)-3-[4-(5-trifluoromethyl-2-pyridyloxy)-phenoxy]-2-butanone,
(138) 2-cyano-2-methylthiomethyl-4-[4-(5-fluoro-2-pyridyloxy)-phenoxy]-3-pentanone,
(140) 2-cyano-2-methylthioethyl-4-[4-(5-trifluoromethyl-2-pyridyloxy)-phenoxy]-3-pentanone,
(142) 1-cyano-1-trifluoromethyl-4-[4-(3-methyl-5-fluoro-2-pyridyloxy)-phenoxy]-2-butanone,
(144) 1-cyano-1-(2,4-dichlorophenyl)-3-[4-(3-chloro-5-trifluoromethyl-2-pyridyloxy)-phenoxy]-3-methyl-2-butanone,
(146) 1-cyano-1-(2,4-dichlorophenyl)-3-[4-(3-methoxycarbonyl-2-pyridyloxy)-phenoxy]-3-methyl-2-butanone,
(148) 1-methylthio-2-cyano-4-[4-(6-trifluoromethyl-2-naphthoxy)-phenoxy]-3-pentanone,
(150) 1-cyano-1-(3-chlorophenyl)-3-[4-(7-trifluoromethyl-2-naphthoxy)-phenoxy]-2-butanone,
(152) 1-cyano-1-(2,4-dichlorophenyl)-3-[4-(6-trifluoromethyl-2-quinolyloxy)-phenoxy]-2-butanone,
(154) 1-cyano-1-(3-trifluoromethylphenyl)-3-[4-(6-trifluoromethyl-2-benzofuranyloxy)-phenoxy]-2-butanone,
(156) 1-cyano-1-(3-trifluoromethylphenyl)-3-[4-(6-chloro-2-benzothienyloxy)-phenoxy]-2-butanone,
(158) 1-cyano-1-[2-(5-methylfurfuryl)-3-[4-(7-methoxy-2-naphthoxy)-phenoxy-2-butanone,
(160) 1-tetrahydrofuryl-2-cyano-4-[4-(6-chloro-2-quinoxalyloxy)-phenoxy]-3-pentanone,
(162) 1-cyano-2-(3-trifluoromethylphenyl)-3-[4-(6-chloro-2-quinoxalinyloxy)-phenoxy]-3-butanone,
(164) 1-cyano-1-(2,4-dichlorophenyl)-3-[4-(6-chloro-2-quinoxalinyloxy)-phenoxy]-3-butanone,
(166) 2-cyano-2-methyl-4-[4-(6-trifluoromethyl-2-quinoxalinyloxy)-phenoxy]-3-butanone,
(168) 1-methyl-3-cyano-5-[4-(6-chloro-3-methyl-2-quinoxalinyloxy)-phenoxy]-4-hexanethione,
(170) 1-cyano-1-(3-trifluoromethylphenyl)-3-[4-(6-trifluoromethyl-3-methoxy-2-quinoxalinyloxy)-phenoxy]-2-butanone,
(172) 1-cyano-1-(naphthyl-3-[4-(6-chloro-4-methyl-2-benzoxazolyloxy)-phenoxy]-acetone,
(174) 2-cyano-2-propenyl-4-[4-(6-trifluoromethyl-2-benzoxazolyloxy)-phenoxy]-3-pentanone,
(176) 1-cyano-1-(2,4-dichlorophenyl)-3-[4-(6-chloro-2-benzoxazolyloxy)-phenoxy]-2-butanone,
(178) 1-cyano-1-(2,4-dichlorophenyl)-3-[4-(4-chloro-6-fluoro-2-benzothiazolyloxy)-phenoxy]-2-butanone,
(180) 1-cyano-1-(2-thieno)-3-[4-(6-chloro-2-benzothiazolyloxy)-phenoxy]-2-butanone,
(182) 1-cyano-2-propynyl-4-[4-(6-trifluoromethyl-2-benzothiazolylthio)-phenoxy]-2-pentanone,
(184) 1,1-dicyano-3-[4-(6-methyl-oxazolo-[5,4-b]-pyridine-2-oxy)-2-methylphenoxy]-acetone,
(186) 1-cyano-1-(2,4,6-trifluorophenyl)-3-[4-(6-chloro-oxazolo[5,4-b]-pyridine-2-oxy)-phenoxy]-3-methyl-2-pentanone,
(188) 1-cyano-1-(2,4-dichlorophenyl)-3-[4-(6-trifluoromethyl-thiazolo[5,4-b]-pyridine-2-oxy)-phenoxy]-2-butanone,
(190) 2-cyano-2-methoxycarbonyl-4-[4-(6-chlorothiazolo[5,4-b]-pyridine-2-oxy)-phenoxy]-4-methyl-3-pentanone,
(192) 1-cyano-1-(3,5-dichlorobenzoyl)-3-[4-(5-bromo-2-benzimidazolyloxy)-phenoxy]-2-butanone,
(194) 1-cyano-1-methylthio-3-[4-(6-difluoromethyl-2-benzimidazolyloxy)-phenoxy]-2-butanone,
(196) 2-cyano-2-methylthiomethyl-4-[4-(N-methyl-5-chloro-2-benzimidazolyloxy)-phenoxy]-2-pentanone,
(198) 3-cyano-3-methyl-5-[4-(N-isopropyl-5-chloro-2-benzimidazolyloxy)-phenoxy]-4-hexanone,
(200) 1-cyano-1-(2-cyclohexenyl)-3-[4-(6-fluoro-2-quinolyloxy)-phenoxy]-2-butanone,
(202) 1-cyano-1-(tetrahydrofurfuryl)-3-[4-(6-trifluoromethyl-2-quinolyloxy)-phenoxy]-2-butanone,
(204) 2-cyano-2-methyl-4-[4-(4-methoxy-6-chloro-7-methyl-2-quinazolinyloxy)-phenoxy]-3-butanone,
(206) 1-cyano-1-(3-trifluoromethylphenyl)-3-[4-(4-ethoxy-7-bromo-2-quinazolinyloxy)-phenoxy]-2-butanone,
(208) 1-cyano-1-isopropoxy-3-[4-(6-chloro-4-quinazolinone-2-oxy)-phenoxy]-2-butanone,
(210) 1-cyano-1-(2-thieno)-3-[4-(6-chloro-4-quinazolinone-2-oxy)-phenoxy]-2-butanone,
(212) 1-cyano-1-ethoxymethyl-3-[4-(7-trifluoromethyl-4-quinazolinone-2-oxy)-phenoxy]-2-butanone,
(214) 1-cyano-1-(2,4-dichlorophenyl)-3-[4-(5-trifluoromethyl-2-thienyloxy)-phenoxy]-2-butanone,
(216) 1-cyano-1-(2,4-dichlorophenyl)-3-[4-(5-nitro-2-pyridyloxy)-phenoxy]acetone,
(218) 1-cyano-1-(2-(6-cyanopyridyl)]-3-[4-(4-methylthiophenoxy)-2,4-dichlorophenoxy]-2-butanone,
(220) 1-cyano-1-[2-(6-methylthiobenzoxazolyl)]-3-[4-(4-methoxycarbonyl-2-chlorophenoxy)-phenoxy]-acetone,
(222) 1-cyano-1-[2-(7-nitroquinolyl)]-3-[4-(4-cyanophenoxy)-phenoxy]-acetone,
(224) 1-cyano-1-[2-(4-cyano-5-methoxycarbonylpyrimidinyl)]-3-[4-(2-chloro-4-bromophenoxy)-phenoxy]-acetone,
(226) 1-cyano-1-phenyl-3-[4-(3-chloro-5-trifluoromethyl-2-pyridyloxy)-phenoxy]-2-butanone,
(228) 1-cyano-1-(3,4-dichlorophenyl)-3-[4-(3-chloro-5-trifluoromethyl-2-pyridyloxy)phenoxy]-2-butanone,
(230) 1-cyano-1-(2-methoxyphenyl)-3-[4-(3-chloro-5-trifluoromethyl-2-pyridyloxy)phenoxy]-2-butanone,
(232) 1-cyano-1-(3-methoxyphenyl)-3-[4-(3-chloro-5-trifluoromethyl-2-pyridyloxy)phenoxy]-2-butanone,
(234) 1-cyano-1-(3-methylphenyl)-3-[4-(3-chloro-5-trifluoromethyl-2-pyridyloxy)phenoxy]-2-butanone,
(236) 1-cyano-1-(3-trifluoromethylphenyl)-3-[4-(5-trifluoromethyl-2-pyridyloxy)phenoxy]-2-butanone,
(238) 1-cyano-1-(2,4-dichlorophenyl)-3-[4-(3-chloro-5-trifluoromethyl-2-pyridyloxy)phenoxy]-2-pentanone, (240) 1-cyano-1-(2,4-dichlorophenyl)-3-[4-(3-chloro-5-trifluoromethyl-2-pyridyloxy)phenoxy]-2-acetone, (242) 1-cyano-1-(2,4-dichlorophenyl)-3-[4-(3-fluoro-5-chloro-2-pyridyloxy)phenoxy]-2-acetone, (244) 1-cyano-1-(2-chloro-4-methylphenyl)-3-[4-(5-bromo-2-pyridyloxy)phenoxy]-2-butanone, (246) 1-cyano-1-(2,4,6-trifluorophenyl)-3-[4-(3-chloro-5-methyl-2-pyridyloxy)phenoxy]-3-methyl-2-butanone, (248) 1-cyano-1-(2,4-dichlorophenyl)-3-[4-(3-fluro-5-trifluoromethyl-2-pyridyloxy)phenoxy]-3-methyl-2-pentanone, (250) 1-cyano-1-(2,4-dichlorophenyl)-3-[4-(5-trifluoromethyl-2-pyridyloxy)phenoxy]-2-acetone, (252) 1-cyano-1-(2,4-dichlorophenyl)-3-[4-(5-nitro-2-pyridyloxy)phenoxy]-2-butanone, (254) 1-cyano-1-(2,4-dichlorophenyl)-3-[4-(5-bromo-2-pyridyloxy)phenoxy]-2-butanone, (256) 1-cyano-1-(2,4-dichlorophenyl)-3-[4-(5-chloro-2-pyridyloxy)phenoxy]-2-butanone, (258) 1-cyano-1-(3-chlorophenyl)-3-[4-(3-chloro-5-trifluoromethyl-2-pyridyloxy)phenoxy]-2-acetone, (260) 1-cyano-1-(3-chlorophenyl)-3-[4-(trifluoromethyl-2-pyridyloxy)phenoxy]-2-acetone, (262) 1-cyano-1-(2,4-dichlorophenyl)-3-[4-(6-ethoxy-2-pyridyloxy)phenoxy]-2-butanone, (264) 1-cyano-1-phenyl-3-(4-phenoxy-phenoxy)-2-butanone, (266) 1-cyano-1-(2,4-dichlorophenyl)-3-(4-phenoxy-phenoxy)-2-butanone, (268) 1-cyano-1-(3-trifluoromethylphenyl)-3-(4-phenoxy-phenoxy)-acetone, (270) 1-cyano-1-(3-cyanophenyl)-3-(4-phenoxy-phenoxy)-2-butanone, (272) 1-cyano-1-(3-nitrophenyl)-3-(4-phenoxy-phenoxy)-2-butanone, (274) 1-cyano-1-(3-ethoxycarbonylphenyl)-3-(4-phenoxy-phenoxy)-acetone, (275) 1-cyano-1-(3-methylthiophenyl)-3-(4-phenoxy-phenoxy)-acetone, (276) 1-cyano-1-(2,4,6-trimethylphenyl)-3-(4-phenoxy-phenoxy)-acetone, (278) 1-cyano-1-(3-methoxyphenyl)-3-(4-phenoxy-phenoxy)-2-butanone, (280) 3-cyano-5-(4-phenoxy-2,3,5,6-tetrachlorophenoxy)-4-hexanone, (282) 1,2-dicyano-4-(4-phenoxy-phenoxy)-3-butanone, (284) 2-cyano-1-(2-tetrahydrofuryl)-4-(4-phenoxy-phenoxy))-3-butanone, (286) 1-cyano-1-benzoyl-3-(4-phenoxy-phenoxy)-acetone, (288) 1-cyano-1-(2-naphthyl)-3-(4-phenoxy-2,3,5-trimethylphenoxy)-acetone, (290) 1-cyano-1-[2-(N-methylpyrrolidyl)]-3-(4-phenoxy-phenoxy)-2-butanone, (292) 1-cyano-1-(2-benzoxazolyl)-3-(4-phenoxy-phenoxy)-acetone, (294) 1-cyano-1-(2-quinolyl)-3-(4-phenoxy-phenoxy)-acetone, (296) 1-cyano-1-(2-pyridyl)-3-[4-(1-naphthoxy)-phenyl]-acetone, (298) 1-cyano-1-(2-quinoxalinyl)-3-[4-(2-chloro-4-trifluoromethylphenoxy)-phenoxy]-2-butanone, (300) 1-cyano-1-(2-pyridyl)-3-[4-(4-methylthiophenoxy)-phenoxy]-acetone, (302) 1-cyano-1-phenyl-3-[4-(2,4-dichlorophenoxy)-phenoxy]-acetone, (304) 1-cyano-1-phenyl-3-[4-(2-chloro-4-trifluoromethylphenoxy)-phenoxy]-acetone, (306) 1-cyano-1-phenyl-3-[4-(3-nitrophenoxy)-phenoxy]-2-butanone, (308) 1-cyano-1-phenyl-3-[4-(3-cyanophenoxy)-phenoxy]-acetone, (310) 1-cyano-1-phenyl-3-[4-(3-methyl-phenoxy)-phenoxy]-acetone, (312) 1-cyano-1-phenyl-3-[4-(2-thienyloxy)-phenoxy]-acetone, (314) 1-cyano-1-(3-trifluoromethylphenyl)-3-[4-(2-furyloxy)-phenoxy]-acetone, (316) 1,2-dicyano-4-{4-[2-(N-methylpyrrolyloxy)]-phenoxy}-3-butanone, (318) 1-cyano-1-(2-benzothiazolyl)-3-{4-[2-(N-methylpyrrolyloxy)]-phenoxy}-3-butanone, (320) 1-cyano-1-(2-quinazolinyl)-3-[4-(2-thienyloxy)-phenoxy]-2-butanone, (322) 1-cyano-1-phenyl-3-[4-(2-benzoxazolyl-oxy)-phenoxy]-acetone, (323) 1-cyano-1-(2,4-dichlorophenyl)-3-[4-(2-oxazolo[5,4-b]pyridine-2-oxy)-phenoxy]-acetone, (324) 2-cyano-4-[4-(2-benzothiazolyloxy)-phenoxy]-3-butanone, (326) 1-cyano-1-benzoyl-3-[4-(2-quinolyloxy)-phenoxy]-acetone, (328) 1-cyano-1-(2-furyl)-3-[4-(2-quinazolinyloxy)-phenoxy]-acetone, (330) 1-cyano-1-(2,4-dichlorophenyl)-3-[4-(3-chloro-5-trifluoromethyl-2-pyridyloxy)-phenoxy]-2-butanone R-enantiomer (asymmetric carbon is the carbon bonded to the phenoxy and methyl groups), (332) 1-cyano-1-(2,4-dichlorophenyl)-3-[4-(3-chloro-5-trifluoromethyl-2-pyridyloxy)-phenoxy]-2-butanone S-enantiomer (asymmetric carbon is the carbon bonded to the phenoxy and methyl groups).

The above compounds are particularly industrially easily produced and have excellent herbicidal activity.

The cyanoketone derivative of the formula (1), provided by the present invention, can be structurally identified by measurements of infrared absorption spectrum (IR), mass spectrum (MS) and $^1$H-nuclear magnetic resonance spectrum ($^1$H-NMR) and elemental analysis. Typical patterns thereof are as follows.

(i) In the measurement of the cyanoketone derivative of the formula (1) for infrared absorption spectrum (IR), a characteristic absorption based on the ether bond is observed at 1,180 to 1,230 cm$^{-1}$, and a characteristic absorption based on the cyano group is observed at 2,210 to 2,220 cm$^{-1}$.

(ii) The cyanoketone derivative of the formula (1) is measured for mass spectrum (MS), and its composition formula corresponding to each peak observed (generally, a value of m/e obtained by dividing an ion molecular weight, m, by a number of charge, e) is calculated, whereby the molecular weight of the cyanoketone compound and the bonding mode of each atomic group in the molecule can be determined. That is, when a sample measured has the formula (1), there are generally observed molecular ion peaks (to be abbreviated as "M+" hereinafter) having strength according to an isotopic abundance depending upon the number of halogen atoms contained in the molecule, and the molecular weight of the sample therefore can be determined. Further, the molecular weight generally appears as a mass number of each ion derived from the sample which has been cleaved in positions indicated by dotted lines in the following formula (7)

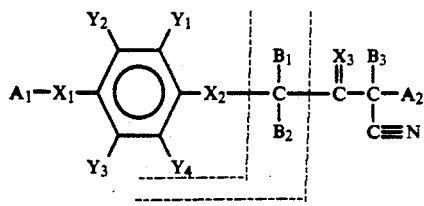
(7)

wherin $A_1$, $X_1$, $X_2$, $X_3$, $Y_1$, $Y_2$, $Y_3$, $Y_4$, $B_1$, $B_2$, $B_3$ and $A_2$ are as defined above.

(iii) The bonding mode of hydrogen bonds in the compound of the present invention, represented by the above formula (1), can be determined by measurement of the compound for $^1$H-nuclear magnetic resonance spectrum ($^1$H-NMR). That is, in the measurement of the compound of the formula (1) in a heavy chloroform solvent, a peak of methine substituted with a cyano group often appears at 5.50 to 5.70 ppm as a multiplet since the carbon atom to which the cyano group is bonded is an assymmetric carbon, and protons on the phenyl group show a multiplet at 6.70 to 7.50 ppm.

(iv) The weight of each of carbon, hydrogen and nitrogen (and halogen if contained) is determined by elemental analysis, and then by deducting the total sum of recognized weight percentages of these elements from 100, the weight percentage of oxygen can be determined. Accordingly, the composition formula of the compound can be determined.

The cyanoketone derivative of the present invention generally is a light yellow or yellowish brown viscous body or solid at room temperature under atmospheric pressure.

The cyanoketone derivative of the present invention is well-dissolved in organic solvents such as benzene, ethyl ether, ethyl alcohol, N,N-dimethylformamide, dimethylsulfoxide, chloroform and carbon tetrachloride. However, it is slightly soluble or insoluble in hexane, heptane and water.

The cyanoketone derivative of the formula (1), provided by the present invention, can be produced by any of the following methods (a), (b) and (c).

(a) A method in which a compound of the following formula (8)

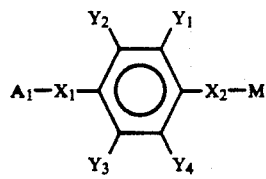
(8)

wherein $A_1$, $X_1$, $X_2$, $Y_1$, $Y_2$, $Y_3$ and $Y_4$ are as defined above, and M is a hydrogen atom or an alkali metal, and a compound of the following formula (9)

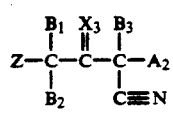
(9)

wherein Z is a halogen atom, and $B_1$, $B_2$, $B_3$, $A_2$ and $X_3$ are as defined in the formula (1), are allowed to react in the presence or absence of a solvent.

(b) A method in which an ester derivative of the following formula (10)

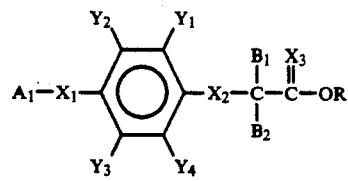
(10)

wherein R is an alkyl group, and $A_1$, $X_1$, $X_2$, $X_3$, $Y_1$, $Y_2$, $Y_3$, $Y_4$, $B_1$ and $B_2$ are as defined in the formula (1), and a cyano derivative of the following formula (11)

(11)

wherein $B_3$ and $A_2$ are as defined in the formula (1), are allowed to react in the presence or absence of a solvent.

(c) A method in which a compound of the following formula (12)

(12)

wherein $A_1$, $X_1$ and M are as defined in the above formula (8), and a compound of the following formula (13)

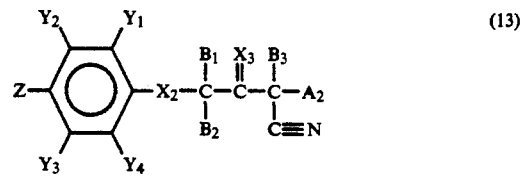
(13)

wherein Z is a halogen atom, and $X_2$, $X_3$, $Y_1$, $Y_2$, $Y_3$, $Y_4$, $B_1$, $B_2$, $B_3$ and $A_2$ are as defined in the formula (1), are allowed to react in the presence or absence of a solvent.

In the above method (a), the feed molar ratio of the compounds of the formulae (8) and (9) may be properly determined as required. In general, these compounds are used in an equimolar amount or one of these is used in a little excess, for example, in an amount that is greater than the amount of the other by not more than 20%.

In the above method (b), the feed molar ratio of the ester derivative of the formula (10) and the cyano derivative of the formula (11) may be properly determined as required. In general, these compounds are used in an equimolar amount or one of these is used in a little excess, for example, in an amount that is greater than the amount of the other by not more than 20%.

In the above method (c), the feed molar ratio of the compounds of the formulae (12) and (13) may be properly determined as required. In general, these compounds are used in an equimolar amount or one of these is used in a little excess, for example, in an amount that is greater than the amount of the other by not more than 20%.

The solvent each in the above methods (a) to (c) is not specially limited, and can be selected from known solvents. Typical examples of the solvent include alcohols such as methanol and ethanol; ethers such as diethyl ether, dimethoxyethane, tetrahydrofuran and dioxane; aromatic solvents such as benzene and toluene, chlorine-containing solvents such as methylene chloride, chloroform and carbon tetrachloride; N,N-dimethylformamide; dimethylsulfoxide; and sulfolane.

In the methods (a) and (c), when M is hydrogen, the co-presence of a hydrogen halide binding agent is preferred in order to bind the hydrogen halide produced as a by-product. The hydrogen halide binding agent is not specially limited, and can be selected from known agents. Typical examples of the hydrogen halide binding agent preferably usable include trialkylamines such as triethylamine, trimethylamine and tripropylamine, pyridine, sodium alcoholate, potassium alcoholate, 1,8-diazabicyclo[5,4,0]-7-undecene, sodium carbonate, potassium carbonate, sodium hydroxide, potassium hydroxide and sodium hydrite.

In the method (b), the condensation agent for removing alcohol from the reaction of the compound of formula (10) with the compound of formula (11) is not specially limited, and can be selected from known agents. Typical examples of the agent include sodium methylate, potassium methylate, sodium ethylate, potassium ethylate and potassium tert-butylate.

In the methods (a) and (c), examples of the alkali metal, represented by M, in the compounds of the formulae (8) and (12) include sodium, potassium and lithium. Of these metals, sodium and potassium are preferred.

In the methods (a) and (c), examples of the halogen atom, represented by Z, in the compounds of the formulae (9) and (13) include fluorine, chlorine, bromine and iodine.

In the method (b), examples of the alkyl group, represented by R, in the ester derivative of the formula (10) include methyl, ethyl, n-propyl, isopropyl, n-butyl, isobutyl, tert-butyl, pentyl, hexyl, heptyl, octyl, nonyl and decyl. Methyl and ethyl are generally preferably used.

In the methods (a), (b) and (c), the reaction is carried out at a temperature in the range of −30 to 200° C., preferably in the range of 5° to 150° C., for 0.5 to 45 hours, preferably 3 to 24 hours.

The method of isolating the intended product, a cyanoketone derivative, from the reaction system and purifying it is not specially limited, and can be selected from known methods. It is generally preferred to employ a method in which the reaction mixture is added to water, the resultant mixture was subjected to extraction with an organic solvent, and after removing the solvent, the remainder is recrystallized or purified by column chromatography.

A study of the present inventors has showed that the novel cyanoketone derivative of the formula (1), provided by the present invention, has herbicidal activity.

According to the present invention, therefore, there is also provided a herbicide containing the cyanoketone derivative of the formula (1) as an effective or active component.

The form for use of the herbicide of the present invention is not specially limited, and can be selected from known forms. For example, it can be used in the form of any one of granules, a dust, an emulsifiable concentrate, a wettable powder, a flowable agent, a tablet, an aerosol and a fuming agent, which are prepared by using an inert solid carrier, a liquid carrier or an emulsification dispersant in combination.

Further, In the preparation of the formulation, there may be incorporated an auxiliary agent such as a wetting agent, a diluent and a surfactant. The herbicide of the present invention can be used in the form of a liquid or a solid to which the above auxiliary agent is properly incorporated. A surfactant is often effective for improvement in the dispersibility of the herbicide in water or an oil.

The above surfactant can be selected from known anionic surfactants, cationic surfactants and nonionic surfactants used for the preparation of general herbicides. Examples of the particularly suitable surfactants include alkylbenzenesulfonic acid, alkylnaphthalenesulfonic acid, fatty acid sulfonate, polyoxyethylene alkylphenyl ether sulfonate, sodium alkylsulfate, sodium lignin sulfonate and polyalkylnaphthalene sulfonate.

Typical examples of the form of the cyanoketone derivative of the formula (1) for use as a herbicide are as follows.

A wettable powder and granules generally contain an inert solid carrier and a surfactant in addition to the active component of the formula (1). The inert solid carrier is generally selected from natural or synthetic inorganic powders. The most preferred are, for example, clays, talc, potassium carbonate, diatomaceous earth and silica. The wettable powder and granules generally contain 1 to 80 parts by weight of the active component, 5 to 98 parts by weight of the inert solid carrier and 1 to 15 parts by weight of the surfactant. Polyvinyl alcohol and sodium carboxymethylcellulose may naturally be incorporated as required.

The emulsifiable concentrate is generally prepared by dissolving the active component and the surfactant in a solvent. The solvent is preferably selected from those which can dissolve the active component. Typical examples of the solvent include xylene, phenoxyethanol, cyclohexane, solvent naphtha, methylnaphthalene and kerosene. The emulsifiable concentrate generally contains 75 to 20 parts by weight of the active component, 10 to 20 parts by weight of the surfactant and 15 to 60 parts by weight of the solvent.

The dust is a product in which the active component is held on a natural or synthetic inorganic powder. The dust is generally prepared by mixing 0.5 to 6 parts by weight of the active component and 99.5 to 94 parts by weight of the inorganic powder.

The flowable agent is a suspension product prepared by suspending the active component insoluble in water, and adding a dispersant to disperse the suspended active component in water. It is the most widely employed embodiment to suspend 20 to 50% by weight of the active component.

The fuming agent is prepared by incorporating a heat generating agent and a heat generation adjuster. The heat generating agent is selected from nitrates, nitrites, guanidine salts and potassium chlorate. The heat generation adjuster is selected from alkali metal salts and potassium nitrates.

The novel cyanoketone derivative of the formula (1) has remakably high herbicidal activity and is effective against a variety of gramineous weeds. Examples of the weeds against which the herbicidal activity is generally effective include upland soil gramineous weeds such as fall panicum, green foxtail, sorghum, wild oat, Japanese brome, water foxtail, annual bluegrass, barnyardgrass, Johnsongrass, quackgrass, southern crabgrass, goosegrass, Italian ryegrass, burmudagrass and knotgrass.

The cyanoketone derivative of the formula (1) is a novel compound which has high selectively, i.e., remarkably high herbicidal activity against gramineous weeds and safety for broad-leaved crops. Therefore, it has characteristic features in that it is completely harmless to crops such as soybean, adzuki bean, peanut, sunflower, cotton, etc., even when it is used in a high dosage. When the compound of the formula (1), provided by the invention, is sprayed as a herbicide to gramineous plants, not only the use of it as a soil-applied herbicide is effective, but the use of it as a foliar-applied herbicide is also effective. Further, when the carbon atom to which the substituents $B_1$ and $B_2$ are bonded is an asymmetric carbon, R-enantiomer works particularly effectively.

In general, the suitable dosage as an active component of the herbicide of the present invention is in the range of 0.05 to 20.0 kg/h, preferably 0.10 to 6.0 kg/h.

The present invention will be explained further in detail hereinafter by reference to Examples. The present invention, however, shall not be limited to these Examples.

EXAMPLE 1

Preparation of 2-cyano-2-methyl-4-[4-(6-trifluoromethyl-2-quinoxalinyloxy)-phenoxy]-3-butanone (Compound No. 166)

2.20 Grams of a potassium salt of 2-cyano-2-methyl-4-(4-hydroxyphenoxy)-3-butanone and 1.69 g of 2-chloro-6-trifluoromethylquinoxaline were refluxed in 50 nl of N,N-dimethylformamide under heat at 100° C. for 4 hours. The reaction mixture was added to water, and after the mixture was subjected to extraction with chloroform, the extract was concentrated. The residue was separated and purified by column chromatography to give 1.67 g of a compound No. 166 which was a light yellow solid (melting point 113°-115° C.). The yield was 47.1%. The compound No. 166 was analyzed, and the results are shown in Tables 1 to 23.

EXAMPLE 2

Preparation of 1-cyano-1-(3-trifluoromethylphenyl)-3-[4-(3-chloro-5-trifluoromethyl-2-pyridyloxy)phenoxy]-2-butanone (Compound No. 132)

3.0 Grams of ethyl 2-[4-(2-chloro-5-trifluoromethyl-2-pyridyloxy)-phenoxy]-propionate and 1.42 g of α-(3-trifluoromethylphenyl)-acetonitrile were added to a solution of 0.37 g of metal sodium in 50 ml of ethanol, and refluxed under heat for 3 hours. The reaction mixture was added to an aqueous solution of dilute hydrochloric acid, and the mixture was subjected to extraction with chloroform, the extract was concentrated. The residue was separated and purified by column chromatography to give 2.28 g of a compound No. 132 which was a light yellow solid (melting point 70°-71° C.). The yield was 56.0%. The compound No. 132 was analyzed, and the results are shown in Tables 1 to 23.

EXAMPLE 3

Preparation of 1-cyano-1(2,4-dichlorophenyl)-3-[4-(6-chloro-2-benzoxazolyloxy)-phenoxy]-2-butanone (Compound No. 176)

2.70 Grams of a potassium salt of 4-(6-chloro-2-benzoxazolyloxy)phenol and 2.48 g of 1-cyano-1-(2,4-dichlorophenyl)-3-chloro-2-butanone were refluxed in 50 ml of N,N-dimethylformamide under heat at 100° C. for 4 hours. The reaction mixture was added to water, and after the mixture was subjected to extraction with chloroform, the extract was concentrated. The residue was separated and purified by column chromatography to give 2.05 g of a compound No. 176 which was a light yellow solid (melting point 93°-94° C.). The yield was 46.9%. The compound No. 176 was analyzed, and the results are shown in Tables 1 to 23.

EXAMPLE 4

Preparation of R- and S-enantiomers of 1-cyano-1-(2,4-dichlorophenyl)-3-[4-(3-chloro-5-trifluoromethyl-2-pyridyloxy)-phenoxy]-2-butanone (Compounds Nos. 330(a) and 332)

The compound No. 118 was separated into R- and S-enantiomers (Compounds Nos. 330(a) and 332) with liquid chromatography using an optical isomer separation column. The compounds Nos. 330(a) and 332 were analyzed, and the results are shown in Tables 1 to 23.

R-enantiomer (Compound No. 330(a))

angle of rotation $[\alpha]_D^{25} = 23.8°$ (C=1, CHCl$_3$)

S-enantiomer (Compound No. 332)

angle of rotation $[\alpha]_D^{25} = -22.9°$ (C=1, CHCl$_3$)

EXAMPLE 5

Preparation of R-enantiomer of 1-cyano-1-(2,4-dichlorophenyl)-3-[4-(3-chloro-5-trifluromethyl-2-pyridyloxy)-phenoxy]-2-butanone (Compound No. 330(b))

3.2 Grams of potassium salt of R-(+)-1-cyano-1-(2,4-dichlorophenyl)-3-(4-hydroxyphenoxy)-2-butanone and 1.8 g of 2,3-dichloro-5-trifluoromethylpyridine were heated in 50 ml of N,N-dimethylformamide at 50° C. for 4 hours. Then, N,N-dimethylformamide was distilled off under reduced pressure, and water was added to the residue. The resultant mixture was subjected to extraction with chloroform, and the extract was concentrated. The residue was separated and purified by column chromatography to give 2.51 g of a compound No. 330(b) which was a white solid (melting point 83°-84° C.). The yield was 56.2%, and the optical purity was 80.0% ee. The compound No. 330(b) was analyzed, and the results are shown in Tables 1 to 23.

EXAMPLE 6

Compounds shown in Tables 1 to 23 were prepared in the same manner as in Example 1, 2 or 3, and analyzed. The results are shown in Tables 1 to 23. In Tables 1 to 23, the infrared absorption spectra show characteristic absorptions based on an ether bond and a cyano group, and the mass spectra show molecule ion peaks (M+) and fragment peaks of the compounds which cleaved in the positions shown in formula (7).

In the column of "Elemental analysis" in Tables 1 to 23, the upper row values show the found and the lower row values, the calculated.

TABLE 1

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | | | ¹H-NMR |
|---|---|---|---|---|---|---|---|---|---|---|---|---|---|---|---|---|---|---|
| 100 | 4-F-C₆H₄ | 3-OCH₃-C₆H₄ | H | H | H | O | O | O | H | H | H | H | 391 (M⁺) 217 203 | 1190 2210 | 70.64 70.58 | 4.55 4.64 | 3.55 3.58 | 3.71–3.83(m, 3H) 4.59(s, 2H) 5.58(s, 1H) 7.00–7.50(m, 12H) |
| 103 | 2-F-4-F-C₆H₃ | —CH₃ | CH₃ | H | CH₃ | O | O | O | H | H | H | H | 345 (M⁺) 249 221 | 1200 2220 | 65.90 66.08 | 5.11 4.96 | 4.10 4.06 | 1.19–2.10(m, 9H) 5.42–5.55(m, 1H) 7.05–7.66(m, 7H) |
| 106 | 3-Cl-5-CF₃-C₆H₃ | 2,4-Cl₂-C₆H₃ | CH₃ | H | H | O | O | O | H | H | H | H | 527 (M⁺) 315 287 | 1210 2220 | 54.51 54.52 | 2.88 2.86 | 2.77 2.65 | 1.30–1.78(m, 3H) 4.60–4.98(m, 1H) 5.38–5.49(m, 1H) 6.89–7.54(m, 10H) |
| 110 | 3-Cl-5-CH₃-C₆H₃ | N-methylpyrrole | CH₃ | H | H | O | O | O | H | H | H | H | 408 (M⁺) 261 233 | 1190 2210 | 67.61 67.56 | 5.03 5.18 | 7.00 6.85 | 1.27–1.91(m, 3H) 2.25(s, 3H) 2.51–2.88(m, 3H) 4.67–4.89(m, 1H) 5.46–5.65(m, 1H) 5.99–7.49(m, 10H) |
| 112 | 3-CH₃-5-CF₃-C₆H₃ | imidazole | CH₃ | CH₃ | H | S | O | O | H | H | H | H | 459 (M⁺) 325 283 | 1190 2210 | 60.15 60.12 | 4.43 4.39 | 9.25 9.15 | 1.50(s, 3H) 1.59(s, 3H) 2.27(s, 3H) 6.00(s, 1H) 6.95–7.71(m, 10H) |

TABLE 2

| Compound No. | A1 | A2 | B1 | B2 | B3 | X1 | X2 | X3 | Y1 | Y2 | Y3 | Y4 | MASS | i.r. (cm⁻¹) (C—O—C, CN) | Elemental analysis C H N | ¹H-NMR |
|---|---|---|---|---|---|---|---|---|---|---|---|---|---|---|---|---|
| 114 | 4-CF₃-phenyl | CN | CH₃ | H | H | S | O | S | H | H | H | H | 406 (M⁺) 297 269 | 1220 2210 | 55.98 3.10 6.97 / 56.15 3.22 6.89 | 1.31–1.81(m, 3H) 4.58–5.12(m, 1H) 5.41–5.54(m, 1H) 6.97–7.64(m, 8H) |
| 116 | 2-F-4-Cl-phenyl | CO₂C₂H₅ | CH₃ | H | H | O | S | O | H | H | H | H | 421 (M⁺) 281 253 | 1200 2210 | 57.05 4.00 3.19 / 56.94 4.06 3.32 | 1.19–1.70(m, 6H) 4.20–4.81(m, 3H) 5.51–5.86(m, 1H) 6.93–7.69(m, 7H) |
| 118 | 3-Cl-5-CF₃-2-pyridyl | 2,4-diCl-phenyl | CH₃ | H | H | O | O | O | H | H | H | H | 528 (M⁺) 316 288 | 1190 2220 | 52.31 2.78 5.31 / 52.15 2.66 5.29 | 1.32–1.79(m, 3H) 4.60–4.99(m, 1H) 5.30–5.61(m, 1H) 6.94–7.53(m, 7H) 7.81–8.80(m, 2H) |
| 132 | 3-Cl-5-CF₃-2-pyridyl | 3-CF₃-phenyl | CH₃ | H | H | O | O | O | H | H | H | H | 528 (M⁺) 316 288 | 1195 2220 | 54.32 3.05 5.40 / 54.51 2.86 5.30 | 1.26–1.82(m, 3H) 4.37–4.99(m, 1H) 5.29–5.67(m, 1H) 6.87–7.80(m, 8H) 7.96–8.25(m, 2H) |
| 134 | 3-Cl-5-CF₃-2-pyridyl | 3-Cl-4-CH₃-phenyl | H | H | H | O | O | S | H | H | H | H | 476 (M⁺) 268 254 | 1200 2220 | 57.92 3.43 5.97 / 57.92 3.38 5.87 | 2.10–2.42(m, 3H) 4.61(s, 2H) 5.76(s, 1H) 6.95–7.45(m, 7H) |

TABLE 3

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 136 | 3-CF₃, 6-pyridyl | 2-Cl, 4-(C(=O)-)phenyl with 2,4-diCl | CH₃ | H | H | O | O | O | H | H | H | H | 522 (M⁺) 282 254 | 1190 2220 | 54.89 3.04 5.43 / 55.08 2.89 5.35 | 1.27-1.81(m, 9H) 4.58-5.12(m, 1H) 5.41-5.43(m, 1H) 6.92-7.64(m, 7H) 7.85-8.42(m, 3H) |
| 138 | 5-F, 6-pyridyl | —CH₂SCH₃ | CH₃ | H | CH₃ | O | O | O | H | H | H | H | 374 (M⁺) 232 204 | 1180 2220 | 61.03 5.40 7.62 / 60.95 5.12 7.48 | 1.15-1.68(m, 9H) 4.21-4.44(m, 2H) 5.50-5.61(m, 1H) 7.10-7.39(m, 4H) 7.88-8.39(m, 3H) |
| 142 | 3-CH₃, 5-F, 6-pyridyl | —CF₃ | CH₃ | H | H | O | O | O | H | H | H | H | 382 (M⁺) 246 218 | 1190 2210 | 56.29 3.39 7.39 / 56.55 3.69 7.33 | 1.22-1.70(m, 3H) 2.51(s, 3H) 5.65-5.72(m, 1H) 6.90-7.35(m, 4H) 7.90-8.27(m, 2H) |
| 144 | 3-Cl, 5-CF₃, 6-pyridyl | 2,4-diCl-phenyl | CH₃ | CH₃ | H | O | O | O | H | H | H | H | 542 (M⁺) 330 288 | 1190 2220 | 53.21 3.11 5.00 / 53.01 2.97 5.15 | 1.48(s, 3H) 1.60(s, 3H) 6.04(s, 1H) 7.12-7.53(m, 7H) |

TABLE 4

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 148 | 6-trifluoromethyl-2-naphthyl | —CH₂SCH₃ | CH₃ | H | H | O | O | O | H | H | H | H | 459 (M⁺) 331 303 | 1210 2220 | 62.56 4.44 3.16 / 62.74 4.39 3.05 | 1.20–1.65(m, 3H) 2.52–2.66(m, 3H) 4.31–4.54(m, 3H) 5.45–5.61(m, 1H) 6.97–8.15(m, 10H) |
| 150 | 7-methyl-2-naphthyl | 3-chlorophenyl | CH₃ | H | H | O | O | S | H | H | H | H | 491 (M⁺) 297 269 | 1220 2210 | 66.03 3.77 2.83 / 65.86 3.89 2.85 | 1.30–1.75(m, 3H) 4.61–4.79(m, 1H) 5.41–5.62(m, 1H) 6.96–8.32(m, 14H) |
| 158 | 7-methoxy-2-naphthyl | 5-methyl-2-furyl | CH₃ | H | H | O | O | O | H | H | H | H | 441 (M⁺) 293 265 | 1200 2210 | 73.40 5.16 3.25 / 73.46 5.25 3.17 | 1.32–1.88(m, 3H) 2.15–2.31(m, 3H) 3.81(s, 3H) 4.62–4.77(m, 1H) 5.51–5.71(m, 1H) 6.99–8.35(m, 12H) |
| 160 | 5-chloro-2-methylpyrimidinyl | tetrahydrofurfuryl | CH₃ | H | H | O | O | O | H | H | H | H | 451 (M⁺) 299 271 | 1210 2220 | 64.05 4.93 9.16 / 63.79 4.91 9.30 | 1.26–2.16(m, 7H) 3.30–3.52(m, 2H) 3.90–4.40(m, 3H) 5.46–5.73(m, 1H) 6.99–8.41(m, 7H) 9.05(s, 1H) |

TABLE 5

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 162 | 4-Cl-pyrimidinyl | 3-CF₃-phenyl | CH₃ | H | H | O | O | O | H | H | H | H | 511 (M⁺) 299 271 | 1190 2220 | 60.83 3.46 8.39 / 61.01 3.35 8.21 | 1.31–1.75(m, 3H) 4.51–4.69(m, 1H) 5.51–5.76(m, 1H) 7.08–8.39(m, 11H) 9.11(s, 1H) |
| 164 | 4-Cl-pyrimidinyl | 2,4-diCl-phenyl | CH₃ | H | H | O | O | O | H | H | H | H | 511 (M⁺) 299 271 | 1240 2220 | 58.55 3.16 8.29 / 58.56 3.15 8.20 | 1.25–1.76(m, 3H) 4.43–4.59(m, 1H) 5.43–5.61(m, 1H) 7.00–8.32(m, 10H) 9.10(s, 1H) |
| 166 | 4-CF₃-pyrimidinyl | —CH₃ | H | H | CH₃ | O | O | O | H | H | H | H | 415 (M⁺) 319 305 | 1190 2220 | 61.00 3.94 10.03 / 60.72 3.88 10.12 | 1.19–2.13(m, 6H) 4.62(s, 2H) 6.95–8.41(m, 7H) 9.03(s, 1H) |
| 168 | 4-Cl-pyrimidinyl (H₃C) | —CH(CH₃)₂ | CH₃ | H | H | O | O | S | H | H | H | H | 438 (M⁺) 312 284 | 1200 2220 | 63.11 4.96 9.29 / 62.93 4.82 9.57 | 1.15–1.79(m, 9H) 2.76(s, 3H) 2.93–3.06(m, 1H) 4.44–4.61(m, 1H) 5.61–5.78(m, 1H) 6.96–8.42(m, 7H) |

TABLE 6

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C=O—C, CN) | Elemental analysis C / H / N | ¹H-NMR |
|---|---|---|---|---|---|---|---|---|---|---|---|---|---|---|---|---|
| 170 | OCH₃ substituted pyridine-pyridine with CF₃ | 3-CF₃-phenyl | CH₃ | H | H | O | O | O | H | H | H | H | 575 (M⁺) 363 335 | 1200 2210 | 58.21 3.09 7.11 / 58.44 3.33 7.30 | 1.26–1.85(m, 3H) 4.31(s, 3H) 4.51–4.76(m, 1H) 5.61–5.76(m, 1H) 6.91–8.54(m, 11H) |
| 172 | 4-CH₃-7-Cl-benzoxazol-2-yl | 2-naphthyl | H | H | H | O | O | O | H | H | H | H | 481 (M⁺) 287 273 | 1220 2210 | 70.03 4.00 5.69 / 69.78 3.77 5.81 | 2.53(s, 3H) 4.64(s, 2H) 5.60(s, 1H) 6.99–8.21(m, 13H) |
| 174 | 6-CF₃-benzoxazol-2-yl | —CH₂CH=CH₂ | CH₃ | H | CH₃ | O | O | O | H | H | H | H | 444 (M⁺) 323 295 | 1210 2210 | 62.35 4.18 6.26 / 62.16 4.31 6.30 | 1.25–2.11(m, 6H) 3.80–4.02(m, 2H) 4.47–4.69(m, 1H) 5.01–6.21(m, 4H) 7.02–8.17(m, 7H) |
| 176 | 6-Cl-benzoxazol-2-yl | 2,4-Cl₂-phenyl | CH₃ | H | H | O | O | O | H | H | H | H | 484 (M⁺) 272 244 | 1190 2220 | 59.26 3.35 5.87 / 59.34 3.11 5.77 | 1.25–1.68(m, 3H) 4.49–4.76(m, 1H) 5.50–5.70(m, 1H) 6.96–8.18(m, 10H) |
| 178 | 4-Cl-5-F-benzothiazol-2-yl | 2,4-Cl₂-phenyl | CH₃ | H | H | O | O | O | H | H | H | H | 502 (M⁺) 290 262 | 1190 2220 | 57.43 2.96 5.55 / 57.22 2.80 5.56 | 1.30–1.70(m, 3H) 4.47–4.80(m, 1H) 5.48–5.70(m, 1H) 7.10–8.32(m, 9H) |

TABLE 7

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C | H | N | ¹H-NMR |
|---|---|---|---|---|---|---|---|---|---|---|---|---|---|---|---|---|---|---|
| 180 | 2-chlorobenzothiazol-6-yl | 2-methylthiophen-5-yl | CH₃ | H | H | O | O | O | H | H | H | H | 454 (M⁺) 304 276 | 1200 2220 | 58.14 58.08 | 3.44 3.32 | 6.03 6.16 | 1.29–1.70(m, 3H) 4.53–4.68(m, 1H) 5.51–5.68(m, 1H) 7.03–8.19(m, 10H) |
| 182 | 2-trifluoromethylbenzothiazol-6-yl | —CH₂C≡CH | CH₃ | H | CH₃ | S | O | O | H | H | H | H | 474 (M⁺) 354 326 | 1210 2210 | 58.26 58.22 | 3.74 3.61 | 5.75 5.90 | 1.19–1.98(m, 6H) 2.20–2.31(m, 1H) 3.46–3.55(m, 2H) 4.49–4.70(m, 1H) 5.61–5.79(m, 1H) 6.96–8.20(m, 7H) |
| 184 | 5-methyloxazolo[4,5-b]pyridin-2-yl | —CN | H | H | H | O | O | O | CH₃ | H | H | H | 362 (M⁺) 269 255 | 1190 2220 | 63.11 62.98 | 4.08 3.90 | 15.53 15.46 | 2.17(s, 3H) 2.78(s, 3H) 4.63(s, 2H) 5.49(s, 1H) 7.03–8.32(m, 5H) |
| 186 | 5-chlorooxazolo[4,5-b]pyridin-2-yl | 3,5-difluorophenyl | CH₃ | C₂H₅ | H | O | O | O | H | H | H | H | 515 (M⁺) 317 261 | 1210 2220 | 58.09 58.21 | 3.41 3.32 | 8.08 8.15 | 1.45(s, 3H) 1.63(s, 3H) 6.06(s, 1H) 6.99–8.22(m, 8H) |

TABLE 8

| Compound No. | $A_1$ | $A_2$ | $B_1$ | $B_2$ | $B_3$ | $X_1$ | $X_2$ | $X_3$ | $Y_1$ | $Y_2$ | $Y_3$ | $Y_4$ | MASS | i.r. (cm$^{-1}$) (C—O—C, CN) | Elemental analysis C / H / N | $^1$H-NMR |
|---|---|---|---|---|---|---|---|---|---|---|---|---|---|---|---|---|
| 188 | thiazolo-pyridine with CF$_3$ | 2,4-dichlorophenyl | CH$_3$ | H | H | O | O | O | H | H | H | H | 539 (M$^+$) 327 299 | 1220 2220 | 51.26 2.75 7.56 / 51.13 2.61 7.78 | 1.28–1.74(m, 3H) 4.50–4.65(m, 1H) 5.53–5.70(m, 1H) 6.94–8.20(m, 9H) |
| 190 | thiazolo-pyridine with Cl | —CO$_2$CH$_3$ | CH$_3$ | CH$_3$ | CH$_3$ | O | O | O | H | H | H | H | 459 (M$^+$) 319 277 | 1190 2210 | 54.73 3.89 9.05 / 54.84 3.94 9.14 | 1.44(s, 3H) 1.64(s, 3H) 2.21(s, 3H) 4.20(s, 3H) 6.94–8.16(m, 6H) |
| 192 | benzimidazole with Br | 3,5-dichlorobenzoyl | Cl | CH$_3$ | H | O | O | O | H | H | H | H | 571 (M$^+$) 331 303 | 1190 2220 | 52.42 2.81 7.46 / 52.38 2.81 7.33 | 1.25–1.81(m, 3H) 4.53–4.66(m, 1H) 5.57–5.73(m, 1H) 7.08–8.31(m, 11H) |
| 194 | benzimidazole with CH$_2$F | —SCH$_3$ | CH$_3$ | H | H | O | O | O | H | H | H | H | 417 (M$^+$) 303 275 | 1170 2220 | 57.62 4.13 10.18 / 57.55 4.10 10.07 | 1.26–1.80(m, 3H) 2.51–2.63(m, 3H) 4.45–4.63(m, 1H) 5.47–5.60(m, 1H) 6.03(t, 1H) 6.93–9.21(m, 8H) |

TABLE 9

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 196 | 6-Cl-1-methyl-2-methylbenzimidazol-yl | —CH₂SCH₃ | CH₃ | H | CH₃ | O | O | O | H | H | H | H | 443 (M⁺) 301 273 | 1200 2220 | 59.36 5.01 9.49 / 59.52 5.00 9.47 | 1.31–1.89(m, 6H) 2.53–2.81(m, 6H) 4.37–4.50(m, 2H) 7.03–8.29(m, 7H) |
| 198 | 6-Cl-1-isopropyl-2-methylbenzimidazol-yl | —CH₂CH₃ | CH₃ | H | CH₃ | O | O | O | H | H | H | H | 439 (M⁺) 329 301 | 1210 2210 | 66.66 6.13 9.37 / 66.52 5.96 9.55 | 1.30–1.79(m, 15H) 2.40–2.80(m, 2H) 3.95–4.19(m, 1H) 4.50–4.80(m, 1H) 7.10–8.35(m, 7H) |
| 200 | 6-F-2-methylquinolin-yl | cyclohexenyl | CH₃ | H | H | O | O | O | H | H | H | H | 430 (M⁺) 268 240 | 1200 2220 | 72.50 5.54 6.29 / 72.54 5.39 6.51 | 1.26–2.47(m, 11H) 4.43–4.70(m, 1H) 5.46–5.69(m, 1H) 6.06–6.21(m, 1H) 7.03–8.33(m, 9H) |
| 202 | 6-CF₃-2-methylquinolin-yl | —CH₂-(tetrahydrofuran-2-yl) | CH₃ | H | H | O | O | O | H | H | H | H | 484 (M⁺) 332 304 | 1190 2220 | 64.17 4.62 5.64 / 64.46 4.79 5.78 | 1.22–2.21(m, 7H) 3.29–3.47(m, 2H) 3.93–4.38(m, 3H) 4.51–4.79(m, 1H) 5.50–5.74(m, 1H) 7.04–8.41(m, 9H) |

TABLE 10

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C / H / N | ¹H-NMR |
|---|---|---|---|---|---|---|---|---|---|---|---|---|---|---|---|---|
| 204 | (3-Cl, 4-CH₃ phenyl with OCH₃ and N) | CH₃ | H | H | CH₃ | O | O | O | H | H | H | H | 409 (M⁺) 313 299 | 1180 2220 | 64.39 4.88 10.38 / 64.47 4.92 10.25 | 1.67–2.03(m, 6H) 2.54(s, 3H) 3.47(s, 3H) 4.62(s, 2H) 7.10–8.30(m, 6H) |
| 206 | (4-Br, 3-CH₃ phenyl with OC₂H₅ and N) | 3-CF₃ phenyl | CH₃ | H | H | O | O | O | H | H | H | H | 599 (M⁺) 387 359 | 1220 2220 | 56.18 3.78 7.26 / 56.01 3.53 7.00 | 1.23–1.87(m, 6H) 4.20–4.60(m, 3H) 5.56–5.79(m, 1H) 6.98–8.31(m, 1H) |
| 208 | (5-Cl phenyl with C=O, NH, N) | —OCH(CH₃)CH₃ | CH₃ | H | H | O | O | O | H | H | H | H | 441 (M⁺) 315 287 | 1180 2220 | 60.03 4.62 9.36 / 59.80 4.56 9.51 | 1.13–1.79(m, 9H) 4.21–4.60(m, 2H) 5.51–5.79(m, 1H) 7.08–8.21(m, 2H) 12.05(bs, 1H) |
| 212 | (4-CF₃ phenyl with C=O, NH, N) | —CH₂OC₂H₅ | CH₃ | H | H | O | O | O | H | H | H | H | 475 (M⁺) 349 321 | 1190 2210 | 57.99 4.08 8.62 / 58.11 4.24 8.84 | 1.09–1.90(m, 6H) 3.52–3.80(m, 4H) 4.43–4.67(m, 1H) 5.60–5.82(m, 1H) 7.08–8.29(m, 7H) 12.09(bs, 1H) |

TABLE 11

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C | H | N | ¹H-NMR |
|---|---|---|---|---|---|---|---|---|---|---|---|---|---|---|---|---|---|---|
| 214 | 5-CF₃-thiophene | 2,4-dichlorophenyl | CH₃ | H | H | O | O | O | H | H | H | H | 499 (M⁺) 287 259 | 1190 2220 | 52.83 52.81 | 2.79 2.82 | 2.90 2.80 | 1.15–1.77(m, 3H) 4.49–4.67(m, 1H) 5.71–5.95(m, 1H) 6.99–7.70(m, 9H) |
| 216 | 5-NO₂-pyridyl | 2,4-dichlorophenyl | H | H | H | O | O | O | H | H | H | H | 457 (M⁺) 245 231 | 1190 2210 | 55.28 55.04 | 2.76 2.86 | 9.30 9.17 | 4.78(s, 2H) 5.64(s, 1H) 7.01–7.44(m, 7H) 8.42–9.00(m, 3H) |
| 218 | 4-SCH₃-phenyl | 6-CN-pyridyl | CH₃ | H | H | O | O | O | Cl | Cl | H | H | 497 (M⁺) 327 299 | 1200 2220 | 58.11 57.84 | 3.27 3.44 | 8.36 8.43 | 1.27–1.91(m, 3H) 2.60(s, 3H) 4.49–4.69(m, 1H) 5.61(s, 1H) 6.97–8.21(m, 9H) |
| 220 | 3-Cl-4-CO₂CH₃-phenyl | 5-SCH₃-benzoxazol-2-yl | H | H | H | O | O | O | H | H | H | H | 522 (M⁺) 291 277 | 1210 2210 | 59.62 59.71 | 3.38 3.66 | 5.35 5.36 | 2.52(s, 3H) 3.96(s, 3H) 4.62(s, 2H) 7.00–8.22(m, 10H) |
| 222 | 4-CN-phenyl | 7-NO₂-2-methylquinolyl | H | H | H | O | O | O | H | H | H | H | 464 (M⁺) 200 186 | 1190 2220 | 67.03 67.24 | 3.44 3.47 | 12.03 12.06 | 4.59(s, 2H) 5.59(s, 1H) 7.09–8.17(m, 13H) |

TABLE 12
| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C | H | N | ¹H-NMR |
|---|---|---|---|---|---|---|---|---|---|---|---|---|---|---|---|---|---|---|
| 224 | 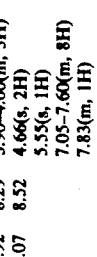 | 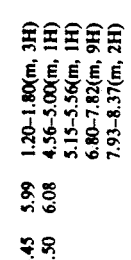 | H | H | H | O | O | O | H | H | H | H | 492 (M⁺) 263 249 | 1190 2220 | 55.88 56.00 | 2.92 3.07 | 8.29 8.52 | 3.90–4.00(m, 3H) 4.66(s, 2H) 5.55(s, 1H) 7.05–7.60(m, 8H) 7.83(m, 1H) |
| 226 | 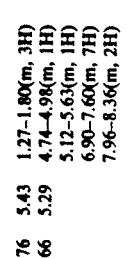 | 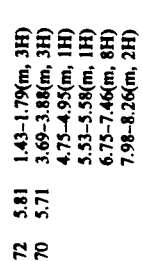 | CH₃ | H | H | O | O | O | H | H | H | H | 460 (M⁺) 316 288 | 1210 2220 | 56.10 55.94 | 3.45 3.50 | 5.99 6.08 | 1.20–1.80(m, 3H) 4.56–5.00(m, 1H) 5.15–5.56(m, 1H) 6.80–7.82(m, 9H) 7.93–8.37(m, 2H) |
| 228 | CF₃, Cl, N (pyridine) | Cl, Cl (dichlorophenyl) | CH₃ | H | H | O | O | O | H | H | H | H | 528 (M⁺) 316 288 | 1190 2210 | 52.40 52.15 | 2.76 2.66 | 5.43 5.29 | 1.27–1.80(m, 3H) 4.74–4.98(m, 1H) 5.12–5.63(m, 1H) 6.90–7.60(m, 7H) 7.96–8.36(m, 2H) |
| 230 | CF₃, Cl, N (pyridine) | OCH₃ (methoxyphenyl) | CH₃ | H | H | O | O | O | H | H | H | H | 490 (M⁺) 316 288 | 1180 2210 | 58.72 58.72 | 3.72 3.70 | 5.81 5.71 | 1.43–1.79(m, 3H) 3.69–3.88(m, 3H) 4.75–4.95(m, 1H) 5.53–5.58(m, 1H) 6.75–7.46(m, 8H) 7.98–8.26(m, 2H) |

TABLE 13

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C / H / N | 1H-NMR |
|---|---|---|---|---|---|---|---|---|---|---|---|---|---|---|---|---|
| 232 | Cl-pyridine-CF₃ (2-methyl) | OCH₃-phenyl (meta) | CH₃ | H | H | O | O | O | H | H | H | H | 490 (M⁺) 316 288 | 1200 2210 | 59.00 3.76 5.66 / 58.72 3.70 5.71 | 1.27–1.80(m, 3H) 3.71–3.83(m, 3H) 4.69–4.92(m, 1H) 5.21–5.54(m, 1H) 6.81–7.36(m, 8H) 7.99–8.27(m, 2H) |
| 234 | Cl-pyridine-CF₃ (2-methyl) | CH₃-phenyl (meta) | CH₃ | H | H | O | O | O | H | H | H | H | 474 (M⁺) 316 288 | 1190 2210 | 60.59 3.85 5.77 / 60.70 3.82 5.90 | 1.26–1.79(m, 3H) 2.15–2.37(m, 3H) 4.66–4.91(m, 1H) 5.20–5.54(m, 1H) 6.68–7.54(m, 8H) 7.99–8.26(m, 2H) |
| 236 | pyridine-CF₃ (2-methyl) | CF₃-phenyl (meta) | CH₃ | H | H | O | O | O | H | H | H | H | 494 (M⁺) 282 254 | 1230 2210 | 58.40 3.26 5.68 / 58.31 3.26 5.67 | 1.26–1.82(m, 3H) 4.44–5.02(m, 1H) 5.40–5.92(m, 1H) 6.87–7.66(m, 8H) 7.96–8.44(m, 3H) |
| 238 | Cl-pyridine-CF₃ (2-methyl) | 2,4-diCl-phenyl | C₂H₅ | H | H | O | O | O | H | H | H | H | 542 (M⁺) 330 288 | 1190 2210 | 52.95 3.07 5.10 / 53.01 2.97 5.15 | 0.85–1.45(m, 3H) 1.76–2.22(m, 2H) 4.69–5.36(m, 1H) 5.57–5.69(m, 1H) 6.80–7.42(m, 7H) 7.99–8.26(m, 2H) |

TABLE 14

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 240 | F, CF₃ pyridine | 2,4-diCl phenyl | H | H | H | O | O | O | H | H | H | H | 514 (M⁺) 302 288 | 1180 2210 | 50.99 2.38 5.56 / 51.24 2.35 5.43 | 4.78(s, 2H) 5.64(s, 1H) 7.01-7.48(m, 7H) 7.99-8.26(m, 2H) |
| 242 | F, Cl pyridine | 2,4-diCl phenyl | H | H | H | O | O | O | H | H | H | H | 464 (M⁺) 252 238 | 1180 2220 | 53.89 2.66 6.05 / 54.16 2.60 6.02 | 4.77(s, 2H) 5.64(s, 1H) 7.01-7.48(m, 7H) 7.99-8.26(m, 2H) |
| 244 | Br pyridine | 2-Cl-4-CH₃ phenyl | CH₃ | H | H | O | O | O | H | H | H | H | 484 (M⁺) 292 264 | 1170 2220 | 56.62 3.67 5.61 / 56.87 3.74 5.77 | 1.27-1.81(m, 3H) 2.10-2.42(m, 3H) 4.58-5.12(m, 1H) 5.41-5.54(m, 1H) 6.92-7.64(m, 7H) 7.85-8.42(m, 3H) |
| 246 | Cl, CH₃ pyridine | 2,6-diF-4-F phenyl | CH₃ | CH₃ | H | O | O | O | H | H | H | H | 474 (M⁺) 276 234 | 1190 2210 | 60.48 3.99 5.77 / 60.70 3.82 5.90 | 1.48(s, 3H) 1.60(s, 3H) 2.13(s, 3H) 6.04(s, 1H) 7.12-7.53(m, 6H) |

TABLE 15

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 248 | 6-methyl-3-CF₃-pyridin-2-yl | 2-Cl, 4-Cl-phenyl (2-methyl) | CH₃ | C₂H₅ | H | O | O | O | H | H | H | H | 540 (M⁺) 328 272 | 1180 2210 | 55.28 3.47 5.31 / 55.47 3.35 5.18 | 0.96–1.30(t, 3H); 1.50(s, 3H); 1.74–2.20(q, 2H); 6.04(s, 1H); 7.12–7.53(m, 7H); 7.98–8.28(m, 2H) |
| 250 | 6-methyl-3-CF₃-pyridin-2-yl | 2-Cl, 4-Cl-phenyl (2-methyl) | H | H | H | O | O | O | H | H | H | H | 480 (M⁺) 268 254 | 1180 2220 | 54.75 2.72 5.63 / 54.91 2.72 5.82 | 4.78(s, 2H); 5.64(s, 1H); 7.01–7.48(m, 7H); 7.85–8.42(m, 3H) |
| 252 | 3-NO₂-6-methyl-pyridin-2-yl | 2-Cl, 4-Cl-phenyl (2-methyl) | CH₃ | H | H | O | O | O | H | H | H | H | 471 (M⁺) 259 231 | 1190 2220 | 55.73 3.29 8.79 / 56.95 3.20 8.90 | 1.30–1.80(m, 3H); 4.61–4.91(m, 1H); 5.28–5.63(m, 1H); 7.01–7.44(m, 7H); 8.42–9.00(m, 3H) |
| 254 | 3-Br-6-methyl-pyridin-2-yl | 2-Cl, 4-Cl-phenyl (2-methyl) | CH₃ | H | H | O | O | O | H | H | H | H | 504 (M⁺) 292 264 | 1170 2220 | 52.01 3.10 5.74 / 52.20 2.99 5.53 | 1.27–1.81(m, 3H); 4.58–5.12(m, 1H); 5.41–5.54(m, 1H); 6.92–7.64(m, 7H); 7.85–8.42(m, 3H) |

TABLE 16

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 256 | 3-Cl, 6-CH₃ pyridyl | 2,4-diCl phenyl | CH₃ | H | H | O | O | O | H | H | H | H | 460 (M⁺) 248 220 | 1170 2220 | 57.00 3.39 6.30<br>57.23 3.28 6.07 | 1.27–1.81(m, 3H)<br>4.58–5.12(m, 1H)<br>5.41–5.54(m, 1H)<br>6.92–7.64(m, 7H)<br>7.85–8.42(m, 3H) |
| 258 | 3-Cl, 5-CF₃, 6-... pyridyl | 3-Cl phenyl | H | H | H | O | O | O | H | H | H | H | 480 (M⁺) 302 288 | 1180 2210 | 55.14 2.66 5.73<br>54.91 2.72 5.82 | 4.78(s, 2H)<br>5.64(s, 1H)<br>7.01–7.52(m, 8H)<br>7.99–8.26(m, 2H) |
| 260 | 5-CF₃ pyridyl | 3-Cl phenyl | H | H | H | O | O | O | H | H | H | H | 446 (M⁺) 268 254 | 1190 2210 | 59.34 3.26 6.32<br>59.14 3.16 6.27 | 4.78(s, 2H)<br>5.64(s, 1H)<br>7.01–7.52(m, 8H)<br>7.99–8.26(m, 2H) |
| 262 | 2-OC₂H₅, 6-CH₃ pyridyl | 2,4-diCl phenyl | CH₃ | H | H | O | O | O | H | H | H | H | 470 (M⁺) 258 230 | 1180 2220 | 61.31 4.36 5.94<br>61.16 4.28 5.94 | 1.27–1.81(m, 3H)<br>4.28–5.12(m, 1H)<br>5.41–5.54(m, 1H)<br>6.92–7.64(m, 7H)<br>7.80–8.39(m, 3H) |
| 264 | phenyl | phenyl | CH₃ | H | H | O | O | O | H | H | H | H | 357 (M⁺) 213 185 | 1200 2210 | 77.50 5.44 3.76<br>77.29 5.36 3.92 | 1.27–1.89(m, 3H)<br>4.61–4.88(m, 1H)<br>5.49–5.73(m, 1H)<br>6.98–7.56(m, 14H) |

TABLE 17

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C | H | N | ¹H-NMR |
|---|---|---|---|---|---|---|---|---|---|---|---|---|---|---|---|---|---|---|
| 266 | phenyl | 2,4-dichlorophenyl | CH₃ | H | H | O | O | O | H | H | H | H | 425 (M⁺) 213 185 | 1220 2220 | 65.00 64.80 | 4.09 4.02 | 3.51 3.29 | 1.25–1.96(m, 3H) 4.72–4.98(m, 1H) 5.48–5.77(m, 1H) 7.00–7.67(m, 12H) |
| 268 | phenyl | 3-CF₃-phenyl | H | H | H | O | O | O | H | H | H | H | 411 (M⁺) 199 185 | 1210 2220 | 67.26 67.15 | 4.06 3.92 | 3.22 3.41 | 4.62(s, 2H) 5.54(s, 1H) 7.05–7.66(m, 13H) |
| 270 | phenyl | 3-CN-phenyl | CH₃ | H | H | O | O | O | H | H | H | H | 382 (M⁺) 213 185 | 1190 2220 | 75.51 75.38 | 4.91 4.74 | 7.08 7.33 | 1.25–1.95(m, 3H) 4.51–4.79(m, 1H) 5.61–5.99(m, 1H) 7.05–7.61(m, 13H) |
| 272 | phenyl | 3-NO₂-phenyl | CH₃ | H | H | O | O | O | H | H | H | H | 402 (M⁺) 213 185 | 1190 2220 | 68.44 68.65 | 4.53 4.51 | 6.99 6.96 | 1.21–1.95(m, 3H) 4.61–4.88(m, 1H) 5.51–5.81(m, 1H) 6.95–7.64(m, 13H) |
| 274 | phenyl | 3-CO₂C₂H₅-phenyl | H | H | H | O | O | O | H | H | H | H | 415 (M⁺) 199 185 | 1200 2220 | 72.22 72.28 | 5.15 5.10 | 3.50 3.37 | 1.30(t, 3H) 4.22(q, 2H) 4.66(s, 2H) 5.54(s, 1H) 7.09–7.66(m, 13H) |

TABLE 18

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C | H | N | ¹H-NMR |
|---|---|---|---|---|---|---|---|---|---|---|---|---|---|---|---|---|---|---|
| 275 | phenyl (with CH₃) | 3-SCH₃-phenyl | H | H | H | O | O | O | H | H | H | H | 389 (M⁺) 199 185 | 1210 2210 | 71.09 70.93 | 4.83 4.92 | 3.55 3.60 | 2.46(s, 3H) 4.53(s, 2H) 5.66(s, 1H) 6.84–7.77(m, 13H) |
| 276 | phenyl (with CH₃) | 3,5-(CH₃)₂-phenyl | H | H | H | O | O | O | H | H | H | H | 385 (M⁺) 199 185 | 1190 2220 | 78.10 77.90 | 6.21 6.02 | 3.56 3.63 | 2.24(s, 9H) 4.63(s, 2H) 5.66(s, 1H) 6.90–7.73(m, 11H) |
| 278 | phenyl (with CH₃) | 3-OCH₃-phenyl | CH₃ | H | H | O | O | O | H | H | H | H | 387 (M⁺) 213 185 | 1210 2220 | 74.51 74.40 | 5.55 5.46 | 3.49 3.62 | 1.26–1.81(m, 3H) 3.71–3.83(m, 3H) 4.54–4.71(m, 1H) 5.46–5.78(m, 1H) 6.81–7.64(m, 11H) |
| 280 | phenyl (with CH₃) | —C₂H₅ | CH₃ | H | H | O | O | O | Cl | Cl | Cl | Cl | 445 (M⁺) 349 321 | 1220 2220 | 50.88 51.04 | 3.35 3.38 | 3.00 3.13 | 1.31–1.73(m, 6H) 2.41–2.76(m, 2H) 4.61–4.91(m, 1H) 5.56–5.97(m, 1H) 6.93–7.51(m, 5H) |
| 282 | phenyl (with CH₃) | —CH₂CN | H | H | H | O | O | O | H | H | H | H | 306 (M⁺) 199 185 | 1210 2210 | 70.38 70.58 | 4.55 4.61 | 9.03 9.15 | 3.81(d, 2H) 4.67(s, 2H) 5.63(s, 1H) 7.00–7.81(m, 9H) |

TABLE 19

| Compound No. | A1 | A2 | B1 | B2 | B3 | X1 | X2 | X3 | Y1 | Y2 | Y3 | Y4 | MASS | i.r. (cm$^{-1}$) (C—O—C, CN) | Elemental analysis C | H | N | $^1$H-NMR |
|---|---|---|---|---|---|---|---|---|---|---|---|---|---|---|---|---|---|---|
| 284 | phenyl | —CH$_2$—(tetrahydrofuran-2-yl) | H | H | H | O | O | O | H | H | H | H | 351 (M$^+$) 199 185 | 1180 2220 | 71.68 71.78 | 6.00 6.02 | 4.12 3.99 | 1.43–2.16(m, 4H) 3.31–3.52(m, 2H) 4.57(s, 2H) 5.55(t, 1H) 6.88–7.69(m, 9H) |
| 286 | phenyl | phenyl | H | H | H | O | O | O | H | H | H | H | 371 (M$^+$) 199 185 | 1190 2220 | 74.23 74.38 | 4.51 4.61 | 3.72 3.77 | 4.60(s, 2H) 5.71(s, 1H) 6.88–7.86(m, 14H) |
| 288 | phenyl | naphthyl | H | H | H | O | O | O | CH$_3$ | CH$_3$ | CH$_3$ | H | 434 (M$^+$) 240 226 | 1220 2220 | 80.06 80.16 | 5.57 5.57 | 3.29 3.22 | 2.22(s, 9H) 4.63(s, 2H) 5.66(s, 1H) 6.81–8.22(m, 13H) |
| 290 | phenyl | N-methylpyrrolyl | CH$_3$ | H | H | O | O | O | H | H | H | H | 360 (M$^+$) 213 185 | 1220 2220 | 73.21 73.32 | 5.73 5.59 | 7.70 7.77 | 1.20–1.78(m, 3H) 2.55–2.83(m, 3H) 4.61–4.82(m, 1H) 5.63–5.83(m, 1H) 6.03–7.71(m, 12H) |
| 292 | phenyl | benzoxazol-2-yl | H | H | H | O | O | O | H | H | H | H | 384 (M$^+$) 199 185 | 1210 2220 | 72.00 71.87 | 4.10 4.20 | 7.36 7.29 | 4.67(s, 2H) 5.68(s, 1H) 6.87–8.22(m, 13H) |

TABLE 20

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C / H / N | ¹H-NMR |
|---|---|---|---|---|---|---|---|---|---|---|---|---|---|---|---|---|
| 294 | phenyl | 2-methylquinolin-yl | H | H | H | O | O | O | H | H | H | H | 394 (M⁺) 199 185 | 1200 2210 | 75.89 4.56 6.95 / 76.13 4.60 7.10 | 4.63(s, 2H) 5.70(s, 1H) 6.83–8.38(m, 15H) |
| 296 | naphthyl | 2-methylpyridin-yl | H | H | H | O | O | O | H | H | H | H | 394 (M⁺) 250 236 | 1180 2220 | 75.81 4.66 7.21 / 76.13 4.60 7.10 | 4.66(s, 2H) 5.65(s, 1H) 6.79–8.39(m, 15H) |
| 298 | 3-chloro-4-(trifluoromethyl)phenyl | 2-methylquinoxalin-yl | CH₃ | H | H | O | O | O | H | H | H | H | 511 (M⁺) 315 287 | 1200 2220 | 60.83 3.08 8.00 / 61.01 3.35 8.21 | 1.25–1.96(m, 3H) 4.61–4.83(m, 1H) 5.63–5.91(m, 1H) 7.00–8.44(m, 11H) 9.08(m, 1H) |
| 300 | 4-(methylthio)phenyl | 2-methylpyridin-yl | H | H | H | O | O | O | H | H | H | H | 390 (M⁺) 246 232 | 1170 2220 | 67.83 4.76 7.05 / 67.67 4.65 7.18 | 2.53(s, 3H) 4.60(s, 2H) 5.69(s, 1H) 6.90–8.29(m, 12H) |
| 302 | 3-chloro-4-methylphenyl | phenyl | H | H | H | O | O | O | H | H | H | H | 411 (M⁺) 267 253 | 1190 2210 | 63.81 3.71 3.29 / 64.09 3.67 3.40 | 4.62(s, 2H) 5.71(s, 1H) 6.85–7.63(m, 12H) |

TABLE 21

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C | H | N | ¹H-NMR |
|---|---|---|---|---|---|---|---|---|---|---|---|---|---|---|---|---|---|---|
| 304 | Cl, CF₃-phenyl | phenyl | H | H | H | O | O | O | H | H | H | H | 445 (M⁺) 301 287 | 1190 2220 | 62.10 61.96 | 3.53 3.39 | 3.27 3.14 | 4.58(s, 2H) 5.63(s, 1H) 6.85–7.70(m, 12H) |
| 306 | NO₂-phenyl | phenyl | CH₃ | H | H | O | O | O | H | H | H | H | 402 (M⁺) 258 230 | 1190 2210 | 68.53 68.65 | 4.43 4.51 | 6.91 6.96 | 4.27–4.81(m, 3H) 4.51–4.79(m, 1H) 5.66–5.92(m, 1H) 6.79–7.78(m, 13H) |
| 308 | CN-phenyl | phenyl | H | H | H | O | O | O | H | H | H | H | 368 (M⁺) 250 236 | 1230 2220 | 75.13 74.99 | 4.21 4.38 | 7.44 7.61 | 4.57(s, 2H) 5.60(s, 1H) 7.00–7.76(m, 13H) |
| 310 | CH₃-phenyl | phenyl | H | H | H | O | O | O | H | H | H | H | 357 (M⁺) 213 199 | 1200 2220 | 77.31 77.29 | 5.25 5.36 | 4.03 3.92 | 2.50(s, 3H) 4.56(s, 2H) 5.66(s, 1H) 6.80–7.65(m, 13H) |
| 312 | thienyl | phenyl | H | H | H | O | O | O | H | H | H | H | 349 (M⁺) 205 191 | 1210 2220 | 68.99 68.75 | 4.21 4.33 | 3.92 4.01 | 4.63(s, 2H) 5.60(s, 1H) 6.73–7.89(m, 12H) |
| 314 | furyl | CF₃-phenyl | H | H | H | O | O | O | H | H | H | H | 401 (M⁺) 189 175 | 1200 2220 | 62.91 62.85 | 3.41 3.52 | 3.63 3.49 | 4.60(s, 2H) 5.59(s, 1H) 6.71–7.77(m, 11H) |

TABLE 22

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 316 | [N-CH₃ pyrrole] | —CH₂CN | H | H | H | O | O | O | Cl | Cl | H | H | 309 (M⁺) 202 188 | 1180 2210 | 65.93 5.10 13.33 / 66.01 4.89 13.59 | 2.23(s, 3H) 3.83(d, 2H) 4.62(s, 2H) 5.63(s, 1H) 6.10–7.67(m, 7H) |
| 318 | [N-CH₃ pyrrole] | [benzothiazole] | CH₃ | H | H | O | O | O | H | H | H | H | 418 (M⁺) 217 189 | 1180 2210 | 66.03 4.87 9.89 / 66.10 4.82 10.04 | 1.25–1.86(m, 3H) 2.22(s, 3H) 4.51–4.83(m, 1H) 5.63–5.91(m, 1H) 5.99–8.22(m, 11H) |
| 320 | [thiophene] | [benzimidazoline] | CH₃ | H | H | O | O | O | H | H | H | H | 415 (M⁺) 219 191 | 1190 2210 | 66.61 4.35 10.01 / 66.49 4.12 10.12 | 1.28–1.95(m, 3H) 4.63–4.93(m, 1H) 5.52–5.85(m, 1H) 6.88–8.46(m, 12H) |
| 322 | [benzoxazole] | [phenyl] | H | H | H | O | O | O | H | H | H | H | 384 (M⁺) 240 226 | 1190 2210 | 72.08 4.05 7.43 / 71.87 4.20 7.29 | 4.60(s, 2H) 5.60(s, 1H) 6.92–8.29(m, 13H) |
| 323 | [oxazolopyridine] | [2,4-dichlorophenyl] | H | H | H | O | O | O | H | H | H | H | 453 (M⁺) 241 227 | 1220 2210 | 58.05 2.81 9.09 / 58.17 2.89 9.25 | 4.58(s, 2H) 5.58(s, 1H) 6.97–8.45(m, 10H) |

TABLE 23

| Compound No. | A₁ | A₂ | B₁ | B₂ | B₃ | X₁ | X₂ | X₃ | Y₁ | Y₂ | Y₃ | Y₄ | MASS | i.r. (cm⁻¹) (C—O—C, CN) | Elemental analysis C H N | ¹H-NMR |
|---|---|---|---|---|---|---|---|---|---|---|---|---|---|---|---|---|
| 324 | benzothiazole | —CH₃ | H | H | H | O | O | O | Cl | Cl | H | H | 338 (M⁺) 256 242 | 1190 2220 | 64.06 4.05 8.21 / 63.89 4.17 8.28 | 2.46(d, 3H) 4.62(s, 2H) 5.70(q, 1H) 6.90–9.29(m, 8H) |
| 326 | quinoline | phenyl-C(=O)- | H | H | H | O | O | O | H | H | H | H | 422 (M⁺) 250 236 | 1200 2210 | 74.12 4.17 6.56 / 73.92 4.30 6.63 | 4.62(s, 2H) 5.72(s, 1H) 6.76–8.42(m, 15H) |
| 328 | quinoline | furyl | H | H | H | O | O | O | H | H | H | H | 385 (M⁺) 251 237 | 1200 2220 | 68.46 4.03 11.09 / 68.57 3.92 10.90 | 4.62(s, 2H) 5.59(s, 1H) 7.02–8.39(m, 12H) |
| 330 (a) | 4-CF₃-6-Cl-pyridyl | 2,4-dichlorophenyl | CH₃ | H | H | O | O | O | H | H | H | H | 528 (M⁺) 316 288 | 1190 2220 | 52.17 2.79 5.40 / 52.15 2.66 5.29 | 1.54(d, 3H) 5.03(q, 1H) 5.56–6.00(m, 1H) 7.00–7.51(m, 7H) 7.89–8.76(m, 2H) |
| 332 | 4-CF₃-6-Cl-pyridyl | 2,4-dichlorophenyl | CH₃ | H | H | O | O | O | H | H | H | H | 528 (M⁺) 316 288 | 1190 2220 | 52.19 2.81 5.37 / 52.15 2.66 5.29 | 1.60(d, 3H) 5.08(q, 1H) 5.37–5.90(m, 1H) 7.05–7.60(m, 7H) 7.88–8.61(m, 2H) |
| 330 (b) | 4-CF₃-6-Cl-pyridyl | 2,4-dichlorophenyl | CH₃ | H | H | O | O | O | H | H | H | H | 528 (M⁺) 316 288 | 1190 2220 | 51.95 2.40 5.08 / 52.15 2.66 5.29 | 1.60(d, 3H) 5.10(q, 1H) 5.56–6.00(m, 1H) 7.07–7.63(m, 7H) 7.77–8.57(m, 2H) |

EXAMPLE 7

Herbicide Preparation Example 1

10 Parts by weight of the above cyanoketone derivative, 2 parts by weight of polyoxyethylene phenyl ether, and 88 parts by weight of finely powdered clay were pulverized and mixed to give a 10% wettable powder.

EXAMPLE 8

Herbicide Preparation Example 2

20 Parts by weight of the above cyanoketone derivative, 70 parts by weight of xylene and 10 parts by weight of a surfactant were mixed and dissolved to give a 20% emulsifiable concentrate.

EXAMPLE 9

Herbicide Preparation Example 3

5 Parts by weight of the above cyanoketone derivative, 50 parts by weight of bentonite and 5 parts by weight of a surfactant were mixed and pulverized to form a paste. The paste was extruded through holes having a diameter of 0.7 mm. and the extrudate was dried and cut to a length of 1 to 2 mm to give 5% granules.

EXAMPLE 10

Herbicidal effect by foliar application

Upland farm soil (clay loom) was filled in 1/1,850-are pots, and seeds of barnyardgrass, green foxtail, blue morningglory, slender amaranth and hairy beggarticks were sown 0.5 to 1 cm deep. When these weeds grown to two- or three-leaf stage, a wetting agent was added to solutions prepared by diluting wettable powders of the compounds with water, and a predetermined amount of each of the mixtures was sprayed to the foliage. After the application, the weeds were allowed to grow in a greenhouse at an average temperature of 25° C. for 2 weeks, and then the herbicidal effects of compounds tested were examined. In addition to compounds of the present invention, the comparative compound of the following formula (14) was also used.

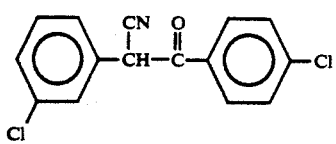
(14)

The results are shown in Tables 24 to 32.

In addition, the above herbicidal effects were evaluated on the basis of the following six ratings, 0 to 5.

0 ... control of weeds 0–9%
1 ... control of weeds 10–29%
2 ... control of weeds 30–49%
3 ... control of weeds 50–69%
4 ... control of weeds 70–89%
5 ... control of weeds 90–100%

TABLE 24

| Compound No. | Active component kg/ha | Barnyardgrass | Green foxtail | Blue morningglory | Slender amaranth | Hairy beggarticks |
|---|---|---|---|---|---|---|
| 100 | 6.0 | 5 | 5 | 0 | 0 | 0 |
|  | 3.0 | 5 | 5 | 0 | 0 | 0 |

TABLE 24-continued

| Compound No. | Active component kg/ha | Barnyardgrass | Green foxtail | Blue morningglory | Slender amaranth | Hairy beggarticks |
|---|---|---|---|---|---|---|
|  | 1.5 | 5 | 5 | 0 | 0 | 0 |
| 103 | 6.0 | 5 | 5 | 0 | 1 | 0 |
|  | 3.0 | 5 | 5 | 0 | 0 | 0 |
|  | 1.5 | 5 | 4 | 0 | 0 | 0 |
| 106 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 110 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 112 | 6.0 | 5 | 5 | 0 | 1 | 0 |
|  | 3.0 | 5 | 5 | 0 | 0 | 0 |
|  | 1.5 | 4 | 5 | 0 | 0 | 0 |
| 114 | 6.0 | 5 | 5 | 1 | 1 | 0 |
|  | 3.0 | 5 | 5 | 0 | 0 | 0 |
|  | 1.5 | 5 | 4 | 0 | 0 | 0 |
| 116 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 118 | 6.0 | 5 | 5 | 1 | 1 | 0 |
|  | 3.0 | 5 | 5 | 0 | 0 | 0 |
|  | 1.5 | 5 | 5 | 0 | 0 | 0 |
| 132 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 134 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 136 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 138 | 6.0 | 5 | 5 | 0 | 0 | 0 |
|  | 3.0 | 5 | 5 | 0 | 0 | 0 |
|  | 1.5 | 5 | 5 | 0 | 0 | 0 |

TABLE 25

| Compound No. | Active component kg/ha | Barnyardgrass | Green foxtail | Blue morningglory | Slender amaranth | Hairy beggarticks |
|---|---|---|---|---|---|---|
| 142 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 144 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 148 | 6.0 | 5 | 5 | 1 | 2 | 0 |
|  | 3.0 | 5 | 5 | 0 | 0 | 0 |
|  | 1.5 | 5 | 5 | 0 | 0 | 0 |
| 150 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 158 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 160 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 162 | 6.0 | 5 | 5 | 1 | 2 | 0 |
|  | 3.0 | 5 | 5 | 0 | 0 | 0 |
|  | 1.5 | 5 | 5 | 0 | 0 | 0 |
| 164 | 6.0 | 5 | 5 | 1 | 1 | 0 |
|  | 3.0 | 5 | 5 | 0 | 0 | 0 |
|  | 1.5 | 5 | 5 | 0 | 0 | 0 |
| 166 | 6.0 | 5 | 5 | 1 | 0 | 0 |
|  | 3.0 | 5 | 5 | 0 | 0 | 0 |
|  | 1.5 | 5 | 5 | 0 | 0 | 0 |
| 168 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 170 | 6.0 | 5 | 5 | 1 | 2 | 0 |
|  | 3.0 | 5 | 5 | 0 | 1 | 0 |
|  | 1.5 | 5 | 5 | 0 | 0 | 0 |

TABLE 25-continued

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 172 | 6.0 | 5 | 5 | 0 | 1 | 0 |
|  | 3.0 | 5 | 5 | 0 | 0 | 0 |
|  | 1.5 | 5 | 5 | 0 | 0 | 0 |

TABLE 26

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 174 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 176 | 6.0 | 5 | 5 | 1 | 2 | 0 |
|  | 3.0 | 5 | 5 | 0 | 1 | 0 |
|  | 1.5 | 5 | 5 | 0 | 0 | 0 |
| 178 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 180 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 182 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 184 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 186 | 6.0 | 5 | 5 | 1 | 1 | 0 |
|  | 3.0 | 5 | 5 | 0 | 0 | 0 |
|  | 1.5 | 5 | 5 | 0 | 0 | 0 |
| 188 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 190 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 192 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 194 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 196 | 6.0 | 5 | 5 | 0 | 0 | 0 |
|  | 3.0 | 5 | 5 | 0 | 0 | 0 |
|  | 1.5 | 5 | 5 | 0 | 0 | 0 |

TABLE 27

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 198 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 200 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 202 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 204 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 206 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 208 | 6.0 | 5 | 5 | 0 | 0 | 0 |
|  | 3.0 | 5 | 5 | 0 | 0 | 0 |
|  | 1.5 | 5 | 5 | 0 | 0 | 0 |

TABLE 27-continued

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 212 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 214 | 6.0 | 5 | 5 | 0 | 0 | 0 |
|  | 3.0 | 5 | 4 | 0 | 0 | 0 |
|  | 1.5 | 4 | 3 | 0 | 0 | 0 |
| 216 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 218 | 6.0 | 5 | 5 | 0 | 2 | 0 |
|  | 3.0 | 5 | 4 | 0 | 1 | 0 |
|  | 1.5 | 4 | 3 | 0 | 0 | 0 |
| 220 | 6.0 | 5 | 5 | 0 | 1 | 0 |
|  | 3.0 | 5 | 5 | 0 | 0 | 0 |
|  | 1.5 | 4 | 4 | 0 | 0 | 0 |
| 222 | 6.0 | 5 | 5 | 0 | 0 | 0 |
|  | 3.0 | 5 | 5 | 0 | 0 | 0 |
|  | 1.5 | 4 | 4 | 0 | 0 | 0 |

TABLE 28

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 224 | 6.0 | 5 | 5 | 1 | 1 | 0 |
|  | 3.0 | 5 | 5 | 0 | 0 | 0 |
|  | 1.5 | 4 | 4 | 0 | 0 | 0 |
| 226 | 6.0 | 5 | 5 | 1 | 2 | 1 |
|  | 3.0 | 5 | 5 | 0 | 0 | 0 |
|  | 1.5 | 5 | 4 | 0 | 0 | 0 |
| 228 | 6.0 | 5 | 5 | 1 | 2 | 1 |
|  | 3.0 | 5 | 5 | 0 | 1 | 0 |
|  | 1.5 | 5 | 4 | 0 | 0 | 0 |
| 230 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 232 | 6.0 | 5 | 5 | 0 | 0 | 0 |
|  | 3.0 | 5 | 4 | 0 | 0 | 0 |
|  | 1.5 | 4 | 3 | 0 | 0 | 0 |
| 234 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 236 | 6.0 | 5 | 5 | 1 | 2 | 0 |
|  | 3.0 | 5 | 5 | 0 | 1 | 0 |
|  | 1.5 | 5 | 5 | 0 | 0 | 0 |
| 238 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 240 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 242 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 244 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 246 | 6.0 | 5 | 5 | 0 | 1 | 0 |
|  | 3.0 | 5 | 5 | 0 | 0 | 0 |
|  | 1.5 | 4 | 4 | 0 | 0 | 0 |

TABLE 29

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 248 | 6.0 | 5 | 5 | 0 | 0 | 0 |
|  | 3.0 | 5 | 5 | 0 | 0 | 0 |
|  | 1.5 | 4 | 4 | 0 | 0 | 0 |

TABLE 29-continued

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 250 | 6.0 | 5 | 5 | 0 | 0 | 0 |
|  | 3.0 | 5 | 4 | 0 | 0 | 0 |
|  | 1.5 | 4 | 3 | 0 | 0 | 0 |
| 252 | 6.0 | 5 | 5 | 0 | 0 | 0 |
|  | 3.0 | 5 | 5 | 0 | 0 | 0 |
|  | 1.5 | 4 | 3 | 0 | 0 | 0 |
| 254 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 256 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 258 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 260 | 6.0 | 5 | 5 | 0 | 0 | 0 |
|  | 3.0 | 5 | 4 | 0 | 0 | 0 |
|  | 1.5 | 4 | 3 | 0 | 0 | 0 |
| 262 | 6.0 | 5 | 5 | 1 | 1 | 0 |
|  | 3.0 | 5 | 5 | 0 | 0 | 0 |
|  | 1.5 | 3 | 3 | 0 | 0 | 0 |
| 264 | 6.0 | 5 | 5 | 1 | 1 | 0 |
|  | 3.0 | 3 | 3 | 0 | 0 | 0 |
|  | 1.5 | 2 | 2 | 0 | 0 | 0 |
| 266 | 6.0 | 5 | 5 | 1 | 0 | 0 |
|  | 3.0 | 4 | 3 | 0 | 0 | 0 |
|  | 1.5 | 3 | 2 | 0 | 0 | 0 |
| 268 | 6.0 | 5 | 5 | 2 | 2 | 1 |
|  | 3.0 | 4 | 4 | 1 | 1 | 0 |
|  | 1.5 | 3 | 3 | 0 | 0 | 0 |
| 270 | 6.0 | 5 | 5 | 1 | 2 | 1 |
|  | 3.0 | 4 | 4 | 0 | 1 | 0 |
|  | 1.5 | 3 | 3 | 0 | 0 | 0 |

TABLE 30

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 272 | 6.0 | 5 | 5 | 1 | 1 | 1 |
|  | 3.0 | 5 | 4 | 0 | 0 | 0 |
|  | 1.5 | 3 | 3 | 0 | 0 | 0 |
| 274 | 6.0 | 5 | 5 | 0 | 0 | 0 |
|  | 3.0 | 4 | 4 | 0 | 0 | 0 |
|  | 1.5 | 3 | 3 | 0 | 0 | 0 |
| 275 | 6.0 | 5 | 5 | 1 | 1 | 0 |
|  | 3.0 | 4 | 4 | 0 | 0 | 0 |
|  | 1.5 | 3 | 3 | 0 | 0 | 0 |
| 276 | 6.0 | 5 | 5 | 0 | 0 | 0 |
|  | 3.0 | 3 | 3 | 0 | 0 | 0 |
|  | 1.5 | 2 | 2 | 0 | 0 | 0 |
| 278 | 6.0 | 5 | 4 | 0 | 0 | 0 |
|  | 3.0 | 4 | 3 | 0 | 0 | 0 |
|  | 1.5 | 3 | 2 | 0 | 0 | 0 |
| 280 | 6.0 | 5 | 5 | 1 | 1 | 1 |
|  | 3.0 | 5 | 5 | 0 | 0 | 0 |
|  | 1.5 | 4 | 4 | 0 | 0 | 0 |
| 282 | 6.0 | 5 | 5 | 0 | 1 | 0 |
|  | 3.0 | 4 | 4 | 0 | 0 | 0 |
|  | 1.5 | 3 | 3 | 0 | 0 | 0 |
| 284 | 6.0 | 5 | 5 | 0 | 1 | 0 |
|  | 3.0 | 5 | 4 | 0 | 0 | 0 |
|  | 1.5 | 3 | 3 | 0 | 0 | 0 |
| 286 | 6.0 | 4 | 4 | 0 | 1 | 0 |
|  | 3.0 | 3 | 3 | 0 | 0 | 0 |
|  | 1.5 | 3 | 2 | 0 | 0 | 0 |
| 288 | 6.0 | 5 | 5 | 0 | 0 | 0 |
|  | 3.0 | 3 | 3 | 0 | 0 | 0 |
|  | 1.5 | 2 | 2 | 0 | 0 | 0 |
| 290 | 6.0 | 5 | 5 | 0 | 1 | 0 |
|  | 3.0 | 4 | 4 | 0 | 0 | 0 |
|  | 1.5 | 3 | 3 | 0 | 0 | 0 |
| 292 | 6.0 | 5 | 5 | 0 | 0 | 0 |

TABLE 30-continued

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
|  | 3.0 | 5 | 4 | 0 | 0 | 0 |
|  | 1.5 | 4 | 3 | 0 | 0 | 0 |

TABLE 31

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 294 | 6.0 | 5 | 5 | 0 | 0 | 0 |
|  | 3.0 | 4 | 4 | 0 | 0 | 0 |
|  | 1.5 | 3 | 3 | 0 | 0 | 0 |
| 296 | 6.0 | 5 | 5 | 1 | 1 | 0 |
|  | 3.0 | 4 | 3 | 0 | 0 | 0 |
|  | 1.5 | 3 | 3 | 0 | 0 | 0 |
| 298 | 6.0 | 5 | 5 | 0 | 1 | 0 |
|  | 3.0 | 5 | 5 | 0 | 0 | 0 |
|  | 1.5 | 5 | 5 | 0 | 0 | 0 |
| 300 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 302 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 304 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 306 | 6.0 | 5 | 5 | 1 | 1 | 0 |
|  | 3.0 | 5 | 4 | 0 | 0 | 0 |
|  | 1.5 | 4 | 3 | 0 | 0 | 0 |
| 308 | 6.0 | 5 | 5 | 0 | 1 | 0 |
|  | 3.0 | 5 | 5 | 0 | 0 | 0 |
|  | 1.5 | 4 | 3 | 0 | 0 | 0 |
| 310 | 6.0 | 5 | 5 | 0 | 0 | 0 |
|  | 3.0 | 4 | 4 | 0 | 0 | 0 |
|  | 1.5 | 3 | 3 | 0 | 0 | 0 |
| 312 | 6.0 | 5 | 5 | 0 | 0 | 0 |
|  | 3.0 | 4 | 4 | 0 | 0 | 0 |
|  | 1.5 | 3 | 3 | 0 | 0 | 0 |
| 314 | 6.0 | 5 | 5 | 0 | 1 | 0 |
|  | 3.0 | 5 | 5 | 0 | 0 | 0 |
|  | 1.5 | 4 | 3 | 0 | 0 | 0 |
| 316 | 6.0 | 5 | 5 | 0 | 1 | 0 |
|  | 3.0 | 5 | 4 | 0 | 0 | 0 |
|  | 1.5 | 4 | 3 | 0 | 0 | 0 |

TABLE 32

Herbicidal effect by foliar application

| Compound No. | Active component kg/ha | Barnyard-grass | Green foxtail | Blue morning-glory | Slender amaranth | Hairy beggar-ticks |
|---|---|---|---|---|---|---|
| 318 | 6.0 | 5 | 5 | 1 | 1 | 0 |
|  | 3.0 | 4 | 4 | 0 | 0 | 0 |
|  | 1.5 | 3 | 3 | 0 | 0 | 0 |
| 320 | 6.0 | 5 | 5 | 0 | 1 | 0 |
|  | 3.0 | 4 | 3 | 0 | 0 | 0 |
|  | 1.5 | 3 | 3 | 0 | 0 | 0 |
| 322 | 6.0 | 5 | 5 | 0 | 0 | 0 |
|  | 3.0 | 5 | 5 | 0 | 0 | 0 |
|  | 1.5 | 5 | 5 | 0 | 0 | 0 |
| 323 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 324 | 6.0 | 5 | 5 | 0 | 0 | 0 |
|  | 3.0 | 5 | 5 | 0 | 0 | 0 |
|  | 1.5 | 5 | 4 | 0 | 0 | 0 |
| 326 | 6.0 | 5 | 5 | 0 | 0 | 0 |
|  | 3.0 | 5 | 5 | 0 | 0 | 0 |
|  | 1.5 | 4 | 4 | 0 | 0 | 0 |
| 328 | 6.0 | 5 | 5 | 0 | 0 | 0 |

TABLE 32-continued

| Compound No. | Active component kg/ha | Barn-yard-grass | Green foxtail | Blue morning-glory | Slender amaranth | Hairy beggar-ticks |
|---|---|---|---|---|---|---|
| | 3.0 | 5 | 5 | 0 | 0 | 0 |
| | 1.5 | 5 | 5 | 0 | 0 | 0 |
| 330 (a) | 6.0 | 5 | 5 | 0 | 0 | 0 |
| | 3.0 | 5 | 5 | 0 | 0 | 0 |
| | 1.5 | 5 | 5 | 0 | 0 | 0 |
| 332 | 6.0 | 0 | 0 | 0 | 0 | 0 |
| | 3.0 | 0 | 0 | 0 | 0 | 0 |
| | 1.5 | 0 | 0 | 0 | 0 | 0 |
| 330 (b) | 6.0 | 5 | 5 | 0 | 0 | 0 |
| | 3.0 | 5 | 5 | 0 | 0 | 0 |
| | 1.5 | 5 | 5 | 0 | 0 | 0 |
| Comp. Ex. | 6.0 | 3 | 4 | 3 | 3 | 2 |
| | 3.0 | 2 | 2 | 2 | 2 | 1 |
| | 1.5 | 1 | 1 | 1 | 1 | 0 |

EXAMPLE 11

Test on phytotoxicity on crops by foliar application

Upland farm soil (clay loom) was filled in 1/8850-are pots, and seeds of soybean, adzuki bean and beet were sown 1.5 to 2 cm deep. When the soybean grown to a primary leaf development stage, the predetermined amount of each of the solutions prepared by diluting each of wettable powders of the compounds with water was sprayed to the foliage. After this application, these crops were allowed to grow in a greenhouse at an average temperature of 25° C. for 2 weeks, and then the phytotoxicity of each of the test compounds on the crops was examined. The results are shown in Tables 33 to 39.

The herbicide injury was evaluated as follows. The ratios of the height and total weight (air-dried weight) of an applied lot to those of an unapplied lot were calculated. The lowest ratios of these factors were taken as 5, and the phytotoxicity was evaluated on the basis of the following six ratings 0 to 5.

0 ... ratio to unapplied lot 100%
1 ... ratio to unapplied lot 90–99%
2 ... ratio to unapplied lot 80–89%
3 ... ratio to unapplied lot 60–79%
4 ... ratio to unapplied lot 40–59%
5 ... ratio to unapplied lot 0–39%

TABLE 33

| Compound No. | Active component kg/ha | Soybeans | Adzuki-bean | Beet |
|---|---|---|---|---|
| 100 | 6.0 | 0 | 0 | 0 |
| | 3.0 | 0 | 0 | 0 |
| 103 | 6.0 | 0 | 0 | 0 |
| | 3.0 | 0 | 0 | 0 |
| 106 | 6.0 | 0 | 0 | 1 |
| | 3.0 | 0 | 0 | 0 |
| 110 | 6.0 | 0 | 0 | 0 |
| | 3.0 | 0 | 0 | 0 |
| 112 | 6.0 | 0 | 0 | 0 |
| | 3.0 | 0 | 0 | 0 |
| 114 | 6.0 | 0 | 0 | 1 |
| | 3.0 | 0 | 0 | 0 |
| 116 | 6.0 | 0 | 0 | 0 |
| | 3.0 | 0 | 0 | 0 |
| 118 | 6.0 | 1 | 0 | 1 |
| | 3.0 | 0 | 0 | 0 |
| 132 | 6.0 | 1 | 1 | 1 |
| | 3.0 | 0 | 0 | 0 |
| 134 | 6.0 | 0 | 0 | 0 |
| 136 | 3.0 | 0 | 0 | 0 |
| | 6.0 | 0 | 0 | 0 |
| 138 | 3.0 | 0 | 0 | 0 |
| | 6.0 | 0 | 0 | 0 |
| 142 | 3.0 | 0 | 0 | 0 |
| | 6.0 | 0 | 0 | 0 |
| 144 | 3.0 | 0 | 0 | 0 |
| | 6.0 | 0 | 0 | 1 |
| 148 | 3.0 | 0 | 0 | 0 |
| | 6.0 | 1 | 0 | 2 |
| 150 | 3.0 | 0 | 0 | 0 |
| | 6.0 | 0 | 0 | 0 |
| | 3.0 | 0 | 0 | 0 |

TABLE 34

| Compound No. | Active component kg/ha | Soybeans | Adzuki-bean | Beet |
|---|---|---|---|---|
| 158 | 6.0 | 0 | 0 | 0 |
| | 3.0 | 0 | 0 | 0 |
| 160 | 6.0 | 0 | 0 | 0 |
| | 3.0 | 0 | 0 | 0 |
| 162 | 6.0 | 2 | 1 | 2 |
| | 3.0 | 0 | 0 | 0 |
| 164 | 6.0 | 2 | 1 | 1 |
| | 3.0 | 0 | 0 | 0 |
| 166 | 6.0 | 1 | 1 | 1 |
| | 3.0 | 0 | 0 | 0 |
| 168 | 6.0 | 0 | 0 | 0 |
| | 3.0 | 0 | 0 | 0 |
| 170 | 6.0 | 0 | 0 | 2 |
| | 3.0 | 0 | 0 | 1 |
| 172 | 6.0 | 0 | 0 | 1 |
| | 3.0 | 0 | 0 | 0 |
| 174 | 6.0 | 0 | 0 | 0 |
| | 3.0 | 0 | 0 | 0 |
| 176 | 6.0 | 1 | 1 | 2 |
| | 3.0 | 0 | 0 | 1 |
| 178 | 6.0 | 0 | 0 | 0 |
| | 3.0 | 0 | 0 | 0 |
| 180 | 6.0 | 0 | 0 | 0 |
| | 3.0 | 0 | 0 | 0 |
| 182 | 6.0 | 0 | 0 | 0 |
| | 3.0 | 0 | 0 | 0 |
| 184 | 6.0 | 0 | 0 | 0 |
| | 3.0 | 0 | 0 | 0 |
| 186 | 6.0 | 0 | 0 | 1 |
| | 3.0 | 0 | 0 | 0 |
| 188 | 6.0 | 1 | 1 | 1 |
| | 3.0 | 0 | 0 | 0 |

TABLE 35

| Compound No. | Active component kg/ha | Soybeans | Adzuki-bean | Beet |
|---|---|---|---|---|
| 190 | 6.0 | 0 | 0 | 0 |
| | 3.0 | 0 | 0 | 0 |
| 192 | 6.0 | 0 | 0 | 0 |
| | 3.0 | 0 | 0 | 0 |
| 194 | 6.0 | 0 | 0 | 0 |
| | 3.0 | 0 | 0 | 0 |
| 196 | 6.0 | 0 | 0 | 0 |
| | 3.0 | 0 | 0 | 0 |
| 198 | 6.0 | 0 | 0 | 1 |
| | 3.0 | 0 | 0 | 0 |
| 200 | 6.0 | 0 | 0 | 0 |
| | 3.0 | 0 | 0 | 0 |
| 202 | 6.0 | 0 | 0 | 0 |
| | 3.0 | 0 | 0 | 0 |
| 204 | 6.0 | 0 | 0 | 0 |

TABLE 35-continued

Phytotoxicity by foliar application

| Compound No. | Active component kg/ha | Soybeans | Adzuki-bean | Beet |
|---|---|---|---|---|
| 206 | 3.0 | 0 | 0 | 0 |
|  | 6.0 | 0 | 0 | 0 |
| 208 | 3.0 | 0 | 0 | 0 |
|  | 6.0 | 0 | 0 | 0 |
| 212 | 3.0 | 0 | 0 | 0 |
|  | 6.0 | 0 | 0 | 1 |
| 214 | 3.0 | 0 | 0 | 0 |
|  | 6.0 | 0 | 0 | 0 |
| 216 | 3.0 | 0 | 0 | 0 |
|  | 6.0 | 0 | 0 | 0 |
| 218 | 3.0 | 0 | 0 | 0 |
|  | 6.0 | 1 | 1 | 1 |
| 220 | 3.0 | 0 | 0 | 0 |
|  | 6.0 | 0 | 0 | 1 |
| 222 | 3.0 | 0 | 0 | 0 |
|  | 6.0 | 0 | 0 | 0 |
|  | 3.0 | 0 | 0 | 0 |

TABLE 36

Phytotoxicity by foliar application

| Compound No. | Active component kg/ha | Soybeans | Adzuki-bean | Beet |
|---|---|---|---|---|
| 224 | 6.0 | 1 | 1 | 1 |
|  | 3.0 | 0 | 0 | 0 |
| 226 | 6.0 | 1 | 0 | 1 |
|  | 3.0 | 0 | 0 | 0 |
| 228 | 6.0 | 1 | 1 | 1 |
|  | 3.0 | 0 | 0 | 0 |
| 230 | 6.0 | 0 | 0 | 0 |
|  | 3.0 | 0 | 0 | 0 |
| 232 | 6.0 | 0 | 0 | 0 |
|  | 3.0 | 0 | 0 | 0 |
| 234 | 6.0 | 2 | 1 | 2 |
|  | 3.0 | 1 | 0 | 0 |
| 236 | 6.0 | 2 | 0 | 1 |
|  | 3.0 | 1 | 0 | 0 |
| 238 | 6.0 | 0 | 0 | 0 |
|  | 3.0 | 0 | 0 | 0 |
| 240 | 6.0 | 0 | 0 | 0 |
|  | 3.0 | 0 | 0 | 0 |
| 242 | 6.0 | 0 | 0 | 0 |
|  | 3.0 | 0 | 0 | 0 |
| 244 | 6.0 | 0 | 0 | 0 |
|  | 3.0 | 0 | 0 | 0 |
| 246 | 6.0 | 0 | 0 | 0 |
|  | 3.0 | 0 | 0 | 0 |
| 248 | 6.0 | 0 | 0 | 0 |
|  | 3.0 | 0 | 0 | 0 |
| 250 | 6.0 | 0 | 0 | 0 |
|  | 3.0 | 0 | 0 | 0 |
| 252 | 6.0 | 0 | 0 | 0 |
|  | 3.0 | 0 | 0 | 0 |
| 254 | 6.0 | 0 | 0 | 0 |
|  | 3.0 | 0 | 0 | 0 |

TABLE 37

Phytotoxicity by foliar application

| Compound No. | Active component kg/ha | Soybeans | Adzuki-bean | Beet |
|---|---|---|---|---|
| 256 | 6.0 | 0 | 0 | 0 |
|  | 3.0 | 0 | 0 | 0 |
| 258 | 6.0 | 0 | 0 | 0 |
|  | 3.0 | 0 | 0 | 0 |
| 260 | 6.0 | 0 | 0 | 0 |
|  | 3.0 | 0 | 0 | 0 |
| 262 | 6.0 | 0 | 1 | 1 |
|  | 3.0 | 0 | 0 | 0 |
| 264 | 6.0 | 1 | 1 | 1 |
|  | 3.0 | 0 | 0 | 0 |
| 266 | 6.0 | 0 | 1 | 1 |

TABLE 37-continued

Phytotoxicity by foliar application

| Compound No. | Active component kg/ha | Soybeans | Adzuki-bean | Beet |
|---|---|---|---|---|
|  | 3.0 | 0 | 0 | 0 |
| 268 | 6.0 | 2 | 1 | 1 |
|  | 3.0 | 0 | 0 | 1 |
| 270 | 6.0 | 1 | 1 | 1 |
|  | 3.0 | 0 | 0 | 0 |
| 272 | 6.0 | 1 | 1 | 1 |
|  | 3.0 | 0 | 0 | 0 |
| 274 | 6.0 | 0 | 0 | 0 |
|  | 3.0 | 0 | 0 | 0 |
| 275 | 6.0 | 1 | 1 | 1 |
|  | 3.0 | 0 | 0 | 0 |
| 276 | 6.0 | 0 | 0 | 0 |
|  | 3.0 | 0 | 0 | 0 |
| 278 | 6.0 | 0 | 0 | 0 |
|  | 3.0 | 0 | 0 | 0 |
| 280 | 6.0 | 0 | 0 | 1 |
|  | 3.0 | 0 | 0 | 0 |
| 282 | 6.0 | 0 | 0 | 1 |
|  | 3.0 | 0 | 0 | 0 |
| 284 | 6.0 | 0 | 0 | 1 |
|  | 3.0 | 0 | 0 | 0 |

TABLE 38

Phytotoxicity by foliar application

| Compound No. | Active component kg/ha | Soybeans | Adzuki-bean | Beet |
|---|---|---|---|---|
| 286 | 6.0 | 0 | 0 | 1 |
|  | 3.0 | 0 | 0 | 0 |
| 288 | 6.0 | 0 | 0 | 0 |
|  | 3.0 | 0 | 0 | 0 |
| 290 | 6.0 | 0 | 0 | 1 |
|  | 3.0 | 0 | 0 | 0 |
| 292 | 6.0 | 0 | 0 | 0 |
|  | 3.0 | 0 | 0 | 0 |
| 294 | 6.0 | 0 | 0 | 0 |
|  | 3.0 | 0 | 0 | 0 |
| 296 | 6.0 | 1 | 1 | 1 |
|  | 3.0 | 0 | 0 | 0 |
| 298 | 6.0 | 1 | 0 | 1 |
|  | 3.0 | 0 | 0 | 0 |
| 300 | 6.0 | 0 | 0 | 0 |
|  | 3.0 | 0 | 0 | 0 |
| 302 | 6.0 | 0 | 0 | 0 |
|  | 3.0 | 0 | 0 | 0 |
| 304 | 6.0 | 0 | 0 | 0 |
|  | 3.0 | 0 | 0 | 0 |
| 306 | 6.0 | 0 | 0 | 0 |
|  | 3.0 | 0 | 0 | 0 |
| 308 | 6.0 | 0 | 0 | 1 |
|  | 3.0 | 0 | 0 | 0 |
| 310 | 6.0 | 0 | 0 | 0 |
|  | 3.0 | 0 | 0 | 0 |
| 312 | 6.0 | 0 | 0 | 0 |
|  | 3.0 | 0 | 0 | 0 |
| 314 | 6.0 | 0 | 0 | 1 |
|  | 3.0 | 0 | 0 | 0 |
| 316 | 6.0 | 1 | 1 | 1 |
|  | 3.0 | 0 | 0 | 0 |

TABLE 39

Phytotoxicity by foliar application

| Compound No. | Active component kg/ha | Soybeans | Adzuki-bean | Beet |
|---|---|---|---|---|
| 318 | 6.0 | 0 | 0 | 2 |
|  | 3.0 | 0 | 0 | 1 |
| 320 | 6.0 | 0 | 0 | 1 |
|  | 3.0 | 0 | 0 | 0 |
| 322 | 6.0 | 0 | 0 | 1 |
|  | 3.0 | 0 | 0 | 0 |
| 323 | 6.0 | 0 | 0 | 1 |

TABLE 39-continued

| Compound No. | Active component kg/ha | Phytotoxicity by foliar application | | |
|---|---|---|---|---|
| | | Soybeans | Adzuki-bean | Beet |
| | 3.0 | 0 | 0 | 0 |
| 324 | 6.0 | 0 | 0 | 1 |
| | 3.0 | 0 | 0 | 0 |
| 326 | 6.0 | 0 | 0 | 0 |
| | 3.0 | 0 | 0 | 0 |
| 328 | 6.0 | 0 | 0 | 1 |
| | 3.0 | 0 | 0 | 0 |
| 330 (a) | 6.0 | 0 | 0 | 0 |
| | 3.0 | 0 | 0 | 0 |
| 332 | 6.0 | 0 | 0 | 0 |
| | 3.0 | 0 | 0 | 0 |
| 330 (b) | 6.0 | 0 | 0 | 0 |
| | 3.0 | 0 | 0 | 0 |

EXAMPLE 12

Test on herbicidal effect by upland farm soil application

Upland farm soil (clay loom) was filled in ⅟₈₅₀-are pots, and seeds of barnyardgrass, green foxtail, slender amaranth and hairy beggarticks were sown 0.5 to 1 cm deep. Then, the predetermined amount of each of the solutions prepared by diluting the wettable powders of the compounds with water was sprayed to the soil. After the application, the weeds were allowed to grow in a greenhouse at an average temperature of 25° C. for 2 weeks, and then the herbicidal effects of the test compounds were examined in the same manner as the above Example 10. The results are shown in Tables 40 to 48.

TABLE 40

| Compound No. | Active component kg/ha | Herbicidal effect by upland soil application | | | |
|---|---|---|---|---|---|
| | | Barnyard-grass | Green foxtail | Slender amaranth | Hairy beggar-ticks |
| 100 | 6.0 | 5 | 5 | 0 | 0 |
| | 3.0 | 5 | 5 | 0 | 0 |
| | 1.5 | 5 | 5 | 0 | 0 |
| 103 | 6.0 | 5 | 5 | 0 | 0 |
| | 3.0 | 5 | 5 | 0 | 0 |
| | 1.5 | 5 | 4 | 0 | 0 |
| 106 | 6.0 | 5 | 5 | 0 | 0 |
| | 3.0 | 5 | 5 | 0 | 0 |
| | 1.5 | 5 | 5 | 0 | 0 |
| 110 | 6.0 | 5 | 5 | 0 | 0 |
| | 3.0 | 5 | 5 | 0 | 0 |
| | 1.5 | 5 | 4 | 0 | 0 |
| 112 | 6.0 | 5 | 5 | 0 | 0 |
| | 3.0 | 5 | 5 | 0 | 0 |
| | 1.5 | 5 | 4 | 0 | 0 |
| 114 | 6.0 | 5 | 5 | 1 | 0 |
| | 3.0 | 5 | 5 | 0 | 0 |
| | 1.5 | 4 | 4 | 0 | 0 |
| 116 | 6.0 | 5 | 5 | 0 | 0 |
| | 3.0 | 5 | 5 | 0 | 0 |
| | 1.5 | 5 | 5 | 0 | 0 |
| 118 | 6.0 | 5 | 5 | 1 | 0 |
| | 3.0 | 5 | 5 | 0 | 0 |
| | 1.5 | 5 | 5 | 0 | 0 |
| 132 | 6.0 | 5 | 5 | 0 | 0 |
| | 3.0 | 5 | 5 | 0 | 0 |
| | 1.5 | 5 | 5 | 0 | 0 |
| 134 | 6.0 | 5 | 5 | 0 | 0 |
| | 3.0 | 5 | 5 | 0 | 0 |
| | 1.5 | 4 | 4 | 0 | 0 |
| 136 | 6.0 | 5 | 5 | 0 | 0 |
| | 3.0 | 5 | 5 | 0 | 0 |
| | 1.5 | 5 | 5 | 0 | 0 |
| 138 | 6.0 | 5 | 5 | 0 | 0 |
| | 3.0 | 5 | 5 | 0 | 0 |
| | 1.5 | 5 | 4 | 0 | 0 |

TABLE 41

| Compound No. | Active component kg/ha | Herbicidal effect by upland soil application | | | |
|---|---|---|---|---|---|
| | | Barnyard-grass | Green foxtail | Slender amaranth | Hairy beggar-ticks |
| 142 | 6.0 | 5 | 5 | 0 | 0 |
| | 3.0 | 5 | 5 | 0 | 0 |
| | 1.5 | 5 | 4 | 0 | 0 |
| 144 | 6.0 | 5 | 5 | 1 | 0 |
| | 3.0 | 5 | 5 | 0 | 0 |
| | 1.5 | 5 | 5 | 0 | 0 |
| 148 | 6.0 | 5 | 5 | 1 | 0 |
| | 3.0 | 5 | 5 | 0 | 0 |
| | 1.5 | 5 | 5 | 0 | 0 |
| 150 | 6.0 | 5 | 5 | 0 | 0 |
| | 3.0 | 5 | 5 | 0 | 0 |
| | 1.5 | 5 | 5 | 0 | 0 |
| 158 | 6.0 | 5 | 5 | 0 | 0 |
| | 3.0 | 5 | 5 | 0 | 0 |
| | 1.5 | 4 | 4 | 0 | 0 |
| 160 | 6.0 | 5 | 5 | 0 | 0 |
| | 3.0 | 5 | 5 | 0 | 0 |
| | 1.5 | 5 | 5 | 0 | 0 |
| 162 | 6.0 | 5 | 5 | 1 | 0 |
| | 3.0 | 5 | 5 | 0 | 0 |
| | 1.5 | 5 | 5 | 0 | 0 |
| 164 | 6.0 | 5 | 5 | 1 | 0 |
| | 3.0 | 5 | 5 | 0 | 0 |
| | 1.5 | 5 | 5 | 0 | 0 |
| 166 | 6.0 | 5 | 5 | 1 | 0 |
| | 3.0 | 5 | 5 | 0 | 0 |
| | 1.5 | 5 | 5 | 0 | 0 |
| 168 | 6.0 | 5 | 5 | 0 | 0 |
| | 3.0 | 5 | 5 | 0 | 0 |
| | 1.5 | 4 | 5 | 0 | 0 |
| 170 | 6.0 | 5 | 5 | 2 | 0 |
| | 3.0 | 5 | 5 | 1 | 0 |
| | 1.5 | 5 | 5 | 0 | 0 |
| 172 | 6.0 | 5 | 5 | 1 | 0 |
| | 3.0 | 5 | 5 | 0 | 0 |
| | 1.5 | 5 | 5 | 0 | 0 |

TABLE 42

| Compound No. | Active component kg/ha | Herbicidal effect by upland soil application | | | |
|---|---|---|---|---|---|
| | | Barnyard-grass | Green foxtail | Slender amaranth | Hairy beggar-ticks |
| 174 | 6.0 | 5 | 5 | 0 | 0 |
| | 3.0 | 5 | 5 | 0 | 0 |
| | 1.5 | 5 | 5 | 0 | 0 |
| 176 | 6.0 | 5 | 5 | 1 | 0 |
| | 3.0 | 5 | 5 | 0 | 0 |
| | 1.5 | 5 | 5 | 0 | 0 |
| 178 | 6.0 | 5 | 5 | 0 | 0 |
| | 3.0 | 5 | 5 | 0 | 0 |
| | 1.5 | 5 | 5 | 0 | 0 |
| 180 | 6.0 | 5 | 5 | 0 | 0 |
| | 3.0 | 5 | 5 | 0 | 0 |
| | 1.5 | 5 | 5 | 0 | 0 |
| 182 | 6.0 | 5 | 5 | 0 | 0 |
| | 3.0 | 5 | 5 | 0 | 0 |
| | 1.5 | 5 | 4 | 0 | 0 |
| 184 | 6.0 | 5 | 5 | 1 | 0 |
| | 3.0 | 5 | 5 | 0 | 0 |
| | 1.5 | 4 | 4 | 0 | 0 |
| 186 | 6.0 | 5 | 5 | 1 | 0 |
| | 3.0 | 5 | 5 | 0 | 0 |
| | 1.5 | 5 | 5 | 0 | 0 |
| 188 | 6.0 | 5 | 5 | 1 | 0 |
| | 3.0 | 5 | 5 | 0 | 0 |
| | 1.5 | 5 | 5 | 0 | 0 |
| 190 | 6.0 | 5 | 5 | 0 | 0 |
| | 3.0 | 5 | 5 | 0 | 0 |
| | 1.5 | 5 | 5 | 0 | 0 |
| 192 | 6.0 | 5 | 5 | 0 | 0 |
| | 3.0 | 5 | 5 | 0 | 0 |
| | 1.5 | 5 | 5 | 0 | 0 |
| 194 | 6.0 | 5 | 5 | 0 | 0 |
| | 3.0 | 5 | 5 | 0 | 0 |
| | 1.5 | 4 | 4 | 0 | 0 |

TABLE 42-continued

| Compound No. | Active component kg/ha | Barnyard-grass | Green foxtail | Slender amaranth | Hairy beggarticks |
|---|---|---|---|---|---|
| 196 | 6.0 | 5 | 5 | 0 | 0 |
|  | 3.0 | 5 | 5 | 0 | 0 |
|  | 1.5 | 5 | 5 | 0 | 0 |

TABLE 43

| Compound No. | Active component kg/ha | Barnyard-grass | Green foxtail | Slender amaranth | Hairy beggarticks |
|---|---|---|---|---|---|
| 198 | 6.0 | 5 | 5 | 1 | 0 |
|  | 3.0 | 5 | 5 | 0 | 0 |
|  | 1.5 | 5 | 5 | 0 | 0 |
| 200 | 6.0 | 5 | 5 | 0 | 0 |
|  | 3.0 | 5 | 5 | 0 | 0 |
|  | 1.5 | 4 | 4 | 0 | 0 |
| 202 | 6.0 | 5 | 5 | 0 | 0 |
|  | 3.0 | 5 | 5 | 0 | 0 |
|  | 1.5 | 4 | 4 | 0 | 0 |
| 204 | 6.0 | 5 | 5 | 0 | 0 |
|  | 3.0 | 5 | 5 | 0 | 0 |
|  | 1.5 | 5 | 5 | 0 | 0 |
| 206 | 6.0 | 5 | 5 | 0 | 0 |
|  | 3.0 | 5 | 5 | 0 | 0 |
|  | 1.5 | 5 | 5 | 0 | 0 |
| 208 | 6.0 | 5 | 5 | 0 | 0 |
|  | 3.0 | 5 | 5 | 0 | 0 |
|  | 1.5 | 5 | 5 | 0 | 0 |
| 212 | 6.0 | 5 | 5 | 0 | 0 |
|  | 3.0 | 5 | 5 | 0 | 0 |
|  | 1.5 | 5 | 5 | 0 | 0 |
| 214 | 6.0 | 5 | 5 | 0 | 0 |
|  | 3.0 | 4 | 4 | 0 | 0 |
|  | 1.5 | 3 | 3 | 0 | 0 |
| 216 | 6.0 | 5 | 5 | 0 | 0 |
|  | 3.0 | 5 | 5 | 0 | 0 |
|  | 1.5 | 5 | 4 | 0 | 0 |
| 218 | 6.0 | 5 | 5 | 2 | 0 |
|  | 3.0 | 5 | 5 | 1 | 0 |
|  | 1.5 | 4 | 4 | 0 | 0 |
| 220 | 6.0 | 5 | 5 | 1 | 0 |
|  | 3.0 | 4 | 5 | 0 | 0 |
|  | 1.5 | 3 | 4 | 0 | 0 |
| 222 | 6.0 | 5 | 5 | 1 | 0 |
|  | 3.0 | 5 | 5 | 0 | 0 |
|  | 1.5 | 4 | 5 | 0 | 0 |

TABLE 44

| Compound No. | Active component kg/ha | Barnyard-grass | Green foxtail | Slender amaranth | Hairy beggarticks |
|---|---|---|---|---|---|
| 224 | 6.0 | 5 | 5 | 0 | 0 |
|  | 3.0 | 5 | 5 | 0 | 0 |
|  | 1.5 | 4 | 4 | 0 | 0 |
| 226 | 6.0 | 5 | 5 | 0 | 0 |
|  | 3.0 | 5 | 5 | 0 | 0 |
|  | 1.5 | 5 | 4 | 0 | 0 |
| 228 | 6.0 | 5 | 5 | 1 | 0 |
|  | 3.0 | 5 | 5 | 0 | 0 |
|  | 1.5 | 5 | 4 | 0 | 0 |
| 230 | 6.0 | 5 | 5 | 0 | 0 |
|  | 3.0 | 5 | 5 | 0 | 0 |
|  | 1.5 | 5 | 4 | 0 | 0 |
| 232 | 6.0 | 5 | 5 | 0 | 0 |
|  | 3.0 | 5 | 5 | 0 | 0 |
|  | 1.5 | 4 | 4 | 0 | 0 |
| 234 | 6.0 | 5 | 5 | 1 | 0 |
|  | 3.0 | 5 | 5 | 0 | 0 |
|  | 1.5 | 5 | 5 | 0 | 0 |
| 236 | 6.0 | 5 | 5 | 1 | 0 |
|  | 3.0 | 5 | 5 | 0 | 0 |
|  | 1.5 | 5 | 5 | 0 | 0 |

TABLE 44-continued

| Compound No. | Active component kg/ha | Barnyard-grass | Green foxtail | Slender amaranth | Hairy beggarticks |
|---|---|---|---|---|---|
| 238 | 6.0 | 5 | 5 | 0 | 0 |
|  | 3.0 | 5 | 5 | 0 | 0 |
|  | 1.5 | 5 | 5 | 0 | 0 |
| 240 | 6.0 | 5 | 5 | 0 | 0 |
|  | 3.0 | 5 | 5 | 0 | 0 |
|  | 1.5 | 5 | 4 | 0 | 0 |
| 242 | 6.0 | 5 | 5 | 0 | 0 |
|  | 3.0 | 5 | 4 | 0 | 0 |
|  | 1.5 | 4 | 3 | 0 | 0 |
| 244 | 6.0 | 5 | 5 | 0 | 0 |
|  | 3.0 | 5 | 5 | 0 | 0 |
|  | 1.5 | 5 | 4 | 0 | 0 |
| 246 | 6.0 | 5 | 5 | 1 | 0 |
|  | 3.0 | 5 | 5 | 0 | 0 |
|  | 1.5 | 4 | 3 | 0 | 0 |

TABLE 45

| Compound No. | Active component kg/ha | Barnyard-grass | Green foxtail | Slender amaranth | Hairy beggarticks |
|---|---|---|---|---|---|
| 248 | 6.0 | 5 | 5 | 0 | 0 |
|  | 3.0 | 5 | 5 | 0 | 0 |
|  | 1.5 | 4 | 4 | 0 | 0 |
| 250 | 6.0 | 5 | 5 | 0 | 0 |
|  | 3.0 | 5 | 5 | 0 | 0 |
|  | 1.5 | 4 | 4 | 0 | 0 |
| 252 | 6.0 | 5 | 5 | 0 | 0 |
|  | 3.0 | 5 | 5 | 0 | 0 |
|  | 1.5 | 4 | 4 | 0 | 0 |
| 254 | 6.0 | 5 | 5 | 0 | 0 |
|  | 3.0 | 5 | 5 | 0 | 0 |
|  | 1.5 | 4 | 3 | 0 | 0 |
| 256 | 6.0 | 5 | 5 | 0 | 0 |
|  | 3.0 | 5 | 5 | 0 | 0 |
|  | 1.5 | 4 | 4 | 0 | 0 |
| 258 | 6.0 | 5 | 5 | 0 | 0 |
|  | 3.0 | 5 | 5 | 0 | 0 |
|  | 1.5 | 4 | 4 | 0 | 0 |
| 260 | 6.0 | 5 | 5 | 0 | 0 |
|  | 3.0 | 5 | 5 | 0 | 0 |
|  | 1.5 | 5 | 5 | 0 | 0 |
| 262 | 6.0 | 5 | 5 | 1 | 0 |
|  | 3.0 | 5 | 5 | 0 | 0 |
|  | 1.5 | 4 | 4 | 0 | 0 |
| 264 | 6.0 | 5 | 5 | 1 | 0 |
|  | 3.0 | 3 | 4 | 0 | 0 |
|  | 1.5 | 2 | 3 | 0 | 0 |
| 266 | 6.0 | 5 | 5 | 2 | 0 |
|  | 3.0 | 4 | 4 | 1 | 0 |
|  | 1.5 | 3 | 3 | 0 | 0 |
| 268 | 6.0 | 5 | 5 | 2 | 0 |
|  | 3.0 | 4 | 4 | 1 | 0 |
|  | 1.5 | 3 | 3 | 0 | 0 |
| 270 | 6.0 | 5 | 5 | 2 | 0 |
|  | 3.0 | 4 | 4 | 1 | 0 |
|  | 1.5 | 3 | 2 | 0 | 0 |

TABLE 46

| Compound No. | Active component kg/ha | Barnyard-grass | Green foxtail | Slender amaranth | Hairy beggarticks |
|---|---|---|---|---|---|
| 272 | 6.0 | 5 | 5 | 1 | 0 |
|  | 3.0 | 4 | 5 | 0 | 0 |
|  | 1.5 | 3 | 3 | 0 | 0 |
| 274 | 6.0 | 4 | 4 | 0 | 0 |
|  | 3.0 | 4 | 4 | 0 | 0 |
|  | 1.5 | 3 | 3 | 0 | 0 |
| 275 | 6.0 | 5 | 5 | 1 | 0 |
|  | 3.0 | 5 | 4 | 0 | 0 |
|  | 1.5 | 3 | 3 | 0 | 0 |

TABLE 46-continued

| Compound No. | Active component kg/ha | Barnyard-grass | Green foxtail | Slender amaranth | Hairy beggar-ticks |
|---|---|---|---|---|---|
| 276 | 6.0 | 4 | 4 | 0 | 0 |
|  | 3.0 | 3 | 3 | 0 | 0 |
|  | 1.5 | 2 | 2 | 0 | 0 |
| 278 | 6.0 | 4 | 4 | 0 | 0 |
|  | 3.0 | 4 | 3 | 0 | 0 |
|  | 1.5 | 2 | 1 | 0 | 0 |
| 280 | 6.0 | 5 | 5 | 1 | 1 |
|  | 3.0 | 4 | 4 | 0 | 0 |
|  | 1.5 | 3 | 3 | 0 | 0 |
| 282 | 6.0 | 5 | 5 | 1 | 0 |
|  | 3.0 | 4 | 4 | 0 | 0 |
|  | 1.5 | 4 | 3 | 0 | 0 |
| 284 | 6.0 | 5 | 5 | 1 | 0 |
|  | 3.0 | 4 | 4 | 0 | 0 |
|  | 1.5 | 3 | 3 | 0 | 0 |
| 286 | 6.0 | 5 | 5 | 0 | 0 |
|  | 3.0 | 3 | 4 | 0 | 0 |
|  | 1.5 | 2 | 3 | 0 | 0 |
| 288 | 6.0 | 5 | 5 | 0 | 0 |
|  | 3.0 | 3 | 3 | 0 | 0 |
|  | 1.5 | 2 | 2 | 0 | 0 |
| 290 | 6.0 | 5 | 5 | 0 | 0 |
|  | 3.0 | 4 | 4 | 0 | 0 |
|  | 1.5 | 2 | 3 | 0 | 0 |
| 292 | 6.0 | 5 | 5 | 0 | 0 |
|  | 3.0 | 4 | 4 | 0 | 0 |
|  | 1.5 | 3 | 2 | 0 | 0 |

TABLE 47

| Compound No. | Active component kg/ha | Barnyard-grass | Green foxtail | Slender amaranth | Hairy beggar-ticks |
|---|---|---|---|---|---|
| 294 | 6.0 | 5 | 5 | 0 | 0 |
|  | 3.0 | 4 | 3 | 0 | 0 |
|  | 1.5 | 3 | 2 | 0 | 0 |
| 296 | 6.0 | 5 | 5 | 1 | 0 |
|  | 3.0 | 4 | 4 | 0 | 0 |
|  | 1.5 | 3 | 3 | 0 | 0 |
| 298 | 6.0 | 5 | 5 | 0 | 0 |
|  | 3.0 | 5 | 5 | 0 | 0 |
|  | 1.5 | 5 | 5 | 0 | 0 |
| 300 | 6.0 | 5 | 5 | 0 | 0 |
|  | 3.0 | 5 | 5 | 0 | 0 |
|  | 1.5 | 4 | 4 | 0 | 0 |
| 302 | 6.0 | 5 | 5 | 0 | 0 |
|  | 3.0 | 5 | 5 | 0 | 0 |
|  | 1.5 | 5 | 4 | 0 | 0 |
| 304 | 6.0 | 5 | 5 | 0 | 0 |
|  | 3.0 | 5 | 5 | 0 | 0 |
|  | 1.5 | 5 | 5 | 0 | 0 |
| 306 | 6.0 | 5 | 5 | 1 | 0 |
|  | 3.0 | 5 | 5 | 0 | 0 |
|  | 1.5 | 4 | 3 | 0 | 0 |
| 308 | 6.0 | 5 | 5 | 1 | 0 |
|  | 3.0 | 4 | 4 | 0 | 0 |
|  | 1.5 | 3 | 3 | 0 | 0 |
| 310 | 6.0 | 5 | 5 | 0 | 0 |
|  | 3.0 | 4 | 4 | 0 | 0 |
|  | 1.5 | 3 | 3 | 0 | 0 |
| 312 | 6.0 | 5 | 5 | 0 | 0 |
|  | 3.0 | 4 | 4 | 0 | 0 |
|  | 1.5 | 3 | 3 | 0 | 0 |
| 314 | 6.0 | 5 | 5 | 2 | 0 |
|  | 3.0 | 5 | 4 | 1 | 0 |
|  | 1.5 | 4 | 3 | 0 | 0 |
| 316 | 6.0 | 5 | 5 | 1 | 0 |
|  | 3.0 | 5 | 5 | 0 | 0 |
|  | 1.5 | 3 | 3 | 0 | 0 |

TABLE 48

| Compound No. | Active component kg/ha | Barnyard-grass | Green foxtail | Slender amaranth | Hairy beggar-ticks |
|---|---|---|---|---|---|
| 318 | 6.0 | 5 | 5 | 0 | 0 |
|  | 3.0 | 5 | 5 | 0 | 0 |
|  | 1.5 | 4 | 4 | 0 | 0 |
| 320 | 6.0 | 5 | 5 | 1 | 0 |
|  | 3.0 | 4 | 4 | 0 | 0 |
|  | 1.5 | 3 | 3 | 0 | 0 |
| 322 | 6.0 | 5 | 5 | 0 | 0 |
|  | 3.0 | 5 | 5 | 0 | 0 |
|  | 1.5 | 4 | 3 | 0 | 0 |
| 323 | 6.0 | 5 | 5 | 0 | 0 |
|  | 3.0 | 5 | 4 | 0 | 0 |
|  | 1.5 | 4 | 3 | 0 | 0 |
| 324 | 6.0 | 5 | 5 | 0 | 0 |
|  | 3.0 | 5 | 5 | 0 | 0 |
|  | 1.5 | 4 | 4 | 0 | 0 |
| 326 | 6.0 | 5 | 5 | 0 | 0 |
|  | 3.0 | 5 | 4 | 0 | 0 |
|  | 1.5 | 4 | 3 | 0 | 0 |
| 328 | 6.0 | 5 | 5 | 0 | 0 |
|  | 3.0 | 5 | 5 | 0 | 0 |
|  | 1.5 | 4 | 4 | 0 | 0 |
| 330 (a) | 6.0 | 5 | 5 | 0 | 0 |
|  | 3.0 | 5 | 5 | 0 | 0 |
|  | 1.5 | 5 | 5 | 0 | 0 |
| 332 | 6.0 | 0 | 0 | 0 | 0 |
|  | 3.0 | 0 | 0 | 0 | 0 |
|  | 1.5 | 0 | 0 | 0 | 0 |
| 330 (b) | 6.0 | 5 | 5 | 0 | 0 |
|  | 3.0 | 5 | 5 | 0 | 0 |
|  | 1.5 | 5 | 5 | 0 | 0 |

According to the present invention, there is provided the novel cyanoketone derivative which exhibits excellent herbicidal activity particularly against gramineous weeds.

What is claimed is:

1. A cyanoketone of the following formula (1)

$$A_1-X_1-\underset{Y_3}{\overset{Y_2}{\bigcirc}}-X_2-\underset{B_2}{\overset{B_1}{C}}-\underset{}{\overset{X_3}{\overset{\|}{C}}}-\underset{C\equiv N}{\overset{B_3}{C}}-A_2 \quad (1)$$

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, substituents of said substituted phenyl, naphthyl, and heterocyclic groups being selected from the group consisting of a halogen atom, an alkyl group having 1 to 4 carbon atoms, a halogenoalkyl group having 1 to 4 carbon atoms, an alkoxy group having 1 to 4 carbon atoms, an alkylthio group having 1 to 4 carbon atoms, and alkoxycarbonyl group having 1 to 6 carbon atoms, a nitro group and a cyano group;

each of $X_1$, $X_2$ and $X_3$ is independently an oxygen or sulfur atom;

each of $B_1$, $B_2$ and $B_3$ is independently a hydrogen atom or an alkyl group having 1 to 6 carbon atoms;

each of $Y_1$, $Y_2$, $Y_3$ and $Y_4$ is independently a hydrogen atom, a halogen atom or an alkyl group having 1 to 6 carbon atoms; and $A_2$ is a substituted or unsubstituted group selected from the group consisting of an alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms and an alkoxycarbonyl group having 1 to 6 carbon atoms, substituents of said substituted groups being selected from the group consisting of a halogen atom, an alkoxy group having 1 to 4 carbon atoms, an alkylthio group having 1 to 4 carbon atoms, a tetrahydrofuryl group and a cyano group; and unsubstituted benzoyl group; a halogen-substituted benzoyl group; a cyano group of the group as defined in $A_1$;

provided that when $B_1$ is a hydrogen atom and $B_2$ is alkyl, the compound of the formula (1) is an R- or S-enantiomer with regard to the asymmetric carbon to which $B_1$ and $B_2$ are bonded or a mixture of these enantiomers.

2. The cyanoketone of claim 1, wherein said 5-membered heterocyclic ring is selected from the group consisting of furyl, thienyl, pyrrolyl, imidazolyl, pyrazolyl, oxazolyl, thiazolyl, isooxazolyl and isothiazolyl.

3. The cyanoketone of claim 1, wherein said 6-membered heterocyclic ring is selected from the group consisting of pyridyl, pyranyl, thiopyranyl, pyrazinyl, pyridinyl and triazinyl.

4. The cyanoketone of claim 1, wherein said 5- and 6-membered heterocyclic fused ring group is selected from the group consisting of benzofuranyl, benzothienyl, indolyl, benzimidazolyl, benzothiazolyl, benzoazolyl, oxazolopyridinyl and thiazolopyridinyl.

5. The cyanoketone of claim 1, wherein said 6- and 6-membered heterocyclic fused ring group is selected from the group consisting of quinolyl, quinoxalinyl and quinazolinyl.

6. A herbicide comprising a herbicidally effective amount of a cyanoketone of claim 1 and an inert carrier.

7. A method of inhibiting the growth of gramineous weeds comprising applying a herbicidally effective amount of the cyanoketone of claim 1 to the locus of weed growth.

8. The method of claim 7, wherein said cyanoketone is applied to the soil.

9. The method of claim 7, wherein said cyanoketone is applied to the foliage of said weeds.

* * * * *